US010383787B2

(12) United States Patent
Rosen et al.

(10) Patent No.: US 10,383,787 B2
(45) Date of Patent: Aug. 20, 2019

(54) TREATMENT APPARATUS FOR REMOVING HEAT FROM SUBCUTANEOUS LIPID-RICH CELLS AND MASSAGING TISSUE

(71) Applicant: Zeltiq Aesthetics, Inc., Pleasanton, CA (US)

(72) Inventors: Jesse Nicasio Rosen, Albany, CA (US); Mitchell E. Levinson, Pleasanton, CA (US)

(73) Assignee: Zeltiq Aesthetics, Inc., Pleasanton, CA (US)

( * ) Notice: Subject to any disclaimer, the term of this patent is extended or adjusted under 35 U.S.C. 154(b) by 0 days.

(21) Appl. No.: 15/815,454

(22) Filed: Nov. 16, 2017

(65) Prior Publication Data

US 2018/0153760 A1 Jun. 7, 2018

Related U.S. Application Data

(63) Continuation of application No. 13/616,633, filed on Sep. 14, 2012, now abandoned, which is a
(Continued)

(51) Int. Cl.
*A61H 9/00* (2006.01)
*A61H 7/00* (2006.01)
(Continued)

(52) U.S. Cl.
CPC ............ *A61H 9/0057* (2013.01); *A61H 7/00* (2013.01); *A61H 7/001* (2013.01); *A61H 7/008* (2013.01);
(Continued)

(58) Field of Classification Search
CPC .......... A61H 7/00; A61H 7/008; A61H 7/001; A61H 9/00; A61H 9/0007; A61H 9/0021;
(Continued)

(56) References Cited

U.S. PATENT DOCUMENTS 681,806 A 9/1901 Mignault et al.
889,810 A 6/1908 Robinson et al.
(Continued)

FOREIGN PATENT DOCUMENTS

AU 2011253768 A1 6/2012
CA 2441489 A1 3/2005
(Continued)

OTHER PUBLICATIONS

"ThermaCool Monopolar Capacitive Radiofrequency, The one choice for nonablative tissue tightening and contouring", Thermage, Inc. Tech Brochure, Nov. 30, 2005, 8 pgs.
(Continued)

*Primary Examiner* — Colin W Stuart
(74) *Attorney, Agent, or Firm* — Perkins Coie LLP

(57) ABSTRACT

A treatment device for removing heat from subcutaneous lipid-rich cells of a subject having an actuator that provides mechanical energy to the tissue. The mechanical energy provided may include a vibratory component that can range between low and ultra-high frequencies, and such energy may include various combinations of two or more frequencies tailored to produce the desired effect on the subcutaneous tissue. Disruption of adipose tissue cooled by an external treatment device may be enhanced by applying mechanical energy to cooled tissue. Furthermore, such mechanical energy may impart a vibratory effect, a massage effect, a pulsatile effect, or combinations thereof on the tissue.

14 Claims, 12 Drawing Sheets

Related U.S. Application Data continuation of application No. 11/750,953, filed on May 18, 2007, now abandoned.

(51) Int. Cl.

| | |
|---|---|
| A61F 7/10 | (2006.01) |
| A61F 7/00 | (2006.01) |
| A61F 7/02 | (2006.01) |
| A61H 23/02 | (2006.01) |

(52) U.S. Cl.
CPC .............. *A61H 9/00* (2013.01); *A61H 9/005* (2013.01); *A61H 9/0007* (2013.01); *A61F 7/10* (2013.01); *A61F 2007/0056* (2013.01); *A61F 2007/0075* (2013.01); *A61F 2007/029* (2013.01); *A61F 2007/0228* (2013.01); *A61H 23/0254* (2013.01); *A61H 23/0263* (2013.01); *A61H 2201/165* (2013.01); *A61H 2201/5082* (2013.01); *A61H 2230/50* (2013.01)

(58) Field of Classification Search
CPC .... A61H 9/005; A61H 9/0057; A61H 9/0071; A61H 2009/0064; A61H 23/00; A61H 23/04; A61F 2007/0056; A61F 2007/0075; A61F 2007/029
See application file for complete search history.

(56) References Cited

U.S. PATENT DOCUMENTS

| | | |
|---|---|---|
| 1,093,868 A | 4/1914 | Leighty |
| 2,052,098 A | 8/1936 | Lockett |
| 2,516,491 A | 7/1950 | Swastek |
| 2,521,780 A | 9/1950 | Dodd et al. |
| 2,726,658 A | 12/1955 | Chessey |
| 2,766,619 A | 10/1956 | Tribus et al. |
| 2,851,602 A | 9/1958 | Cramwinckel et al. |
| 3,093,135 A | 6/1963 | Hirschhorn |
| 3,132,688 A | 5/1964 | Nowak |
| 3,133,539 A | 5/1964 | Eidus et al. |
| 3,282,267 A | 11/1966 | Eidus |
| 3,502,080 A | 3/1970 | Hirschhorn |
| 3,516,411 A | 6/1970 | Adler |
| 3,587,577 A | 6/1971 | Zubkov et al. |
| 3,591,645 A | 7/1971 | Selwitz |
| 3,692,338 A | 9/1972 | Nick |
| 3,703,897 A | 11/1972 | Mack et al. |
| 3,710,784 A | 1/1973 | Taylor |
| 3,786,814 A | 1/1974 | Armao |
| 3,827,436 A | 8/1974 | Andera et al. |
| 3,841,323 A | 10/1974 | Stoughton |
| 3,942,519 A | 3/1976 | Shock |
| 3,948,269 A | 4/1976 | Zimmer |
| 3,986,385 A | 10/1976 | Johnston et al. |
| 3,993,053 A | 11/1976 | Grossan |
| 4,002,221 A | 1/1977 | Buchalter |
| 4,026,299 A | 5/1977 | Sauder |
| 4,140,130 A | 2/1979 | Storm |
| 4,149,529 A | 4/1979 | Copeland et al. |
| 4,178,429 A | 12/1979 | Scheffer |
| 4,202,336 A | 5/1980 | Van Gerven |
| 4,266,043 A | 5/1981 | Fujii et al. |
| 4,269,068 A | 5/1981 | Molina |
| 4,381,009 A | 4/1983 | Del Bon |
| 4,396,011 A | 8/1983 | Mack et al. |
| 4,459,854 A | 7/1984 | Richardson et al. |
| 4,470,263 A | 9/1984 | Lehovec et al. |
| 4,483,341 A | 11/1984 | Witteles |
| 4,528,979 A | 7/1985 | Marchenko et al. |
| 4,531,524 A | 7/1985 | Mioduski |
| 4,548,212 A | 10/1985 | Leung |
| 4,555,313 A | 11/1985 | Duchane et al. |
| 4,585,002 A | 4/1986 | Kissin |
| 4,603,076 A | 7/1986 | Bowditch et al. |
| 4,614,191 A | 9/1986 | Perler et al. |
| 4,644,955 A | 2/1987 | Mioduski |
| 4,664,110 A | 5/1987 | Schanzlin |
| 4,700,701 A | 10/1987 | Montaldi |
| 4,718,429 A | 1/1988 | Smidt |
| 4,741,338 A | 5/1988 | Miyamae |
| 4,748,973 A | 6/1988 | Cho |
| 4,758,217 A | 7/1988 | Gueret |
| 4,764,463 A | 8/1988 | Mason et al. |
| 4,802,475 A | 2/1989 | Weshahy |
| 4,832,022 A | 5/1989 | Tjulkov et al. |
| 4,846,176 A | 7/1989 | Golden |
| 4,850,340 A | 7/1989 | Onishi |
| 4,869,250 A | 9/1989 | Bitterly |
| 4,880,564 A | 11/1989 | Abel et al. |
| 4,905,697 A | 3/1990 | Heggs et al. |
| 4,906,463 A | 3/1990 | Cleary et al. |
| 4,930,317 A | 6/1990 | Klein |
| 4,935,345 A | 6/1990 | Guilbeau et al. |
| 4,961,422 A | 10/1990 | Marchosky et al. |
| 4,962,761 A | 10/1990 | Golden |
| 4,990,144 A | 2/1991 | Blott et al. |
| 5,007,433 A | 4/1991 | Hermsdoerffer et al. |
| 5,018,521 A | 5/1991 | Campbell et al. |
| 5,024,650 A | 6/1991 | Hagiwara et al. |
| 5,065,752 A | 11/1991 | Sessions et al. |
| 5,069,208 A | 12/1991 | Noppel et al. |
| 5,084,671 A | 1/1992 | Miyata et al. |
| 5,108,390 A | 4/1992 | Potocky et al. |
| 5,119,674 A | 6/1992 | Nielsen |
| 5,139,496 A | 8/1992 | Hed |
| 5,143,063 A | 9/1992 | Fellner |
| 5,148,804 A | 9/1992 | Hill et al. |
| 5,158,070 A | 10/1992 | Dory |
| 5,169,384 A | 12/1992 | Bosniak et al. |
| 5,197,466 A | 3/1993 | Marchosky et al. |
| 5,207,674 A | 5/1993 | Hamilton |
| 5,221,726 A | 6/1993 | Dabi et al. |
| 5,264,234 A | 11/1993 | Windhab et al. |
| 5,277,030 A | 1/1994 | Miller |
| 5,314,423 A | 5/1994 | Seney et al. |
| 5,327,886 A | 7/1994 | Chiu |
| 5,330,745 A | 7/1994 | Mcdow et al. |
| 5,333,460 A | 8/1994 | Lewis et al. |
| 5,334,131 A | 8/1994 | Omandam et al. |
| 5,336,616 A | 8/1994 | Livesey et al. |
| 5,339,541 A | 8/1994 | Owens |
| 5,342,617 A | 8/1994 | Gold et al. |
| 5,351,677 A | 10/1994 | Kami et al. |
| 5,358,467 A | 10/1994 | Milstein et al. |
| 5,362,966 A | 11/1994 | Rosenthal et al. |
| 5,363,347 A | 11/1994 | Nguyen |
| 5,372,608 A | 12/1994 | Johnson |
| 5,386,837 A | 2/1995 | Sterzer |
| 5,411,541 A | 5/1995 | Bell et al. |
| 5,427,772 A | 6/1995 | Hagan et al. |
| 5,433,717 A | 7/1995 | Rubinsky et al. |
| 5,456,703 A | 10/1995 | Beeuwkes, III et al. |
| 5,472,416 A | 12/1995 | Blugerman et al. |
| 5,486,207 A | 1/1996 | Mahawili |
| 5,497,596 A | 3/1996 | Zatkulak |
| 5,501,655 A | 3/1996 | Rolt et al. |
| 5,505,726 A | 4/1996 | Meserol |
| 5,505,730 A | 4/1996 | Edwards et al. |
| 5,507,790 A | 4/1996 | Weiss |
| 5,514,105 A | 5/1996 | Goodman, Jr. et al. |
| 5,514,170 A | 5/1996 | Mauch |
| 5,516,505 A | 5/1996 | McDow |
| 5,531,742 A | 7/1996 | Barken |
| 5,562,604 A | 10/1996 | Yablon et al. |
| 5,571,801 A | 11/1996 | Segall et al. |
| 5,575,812 A | 11/1996 | Owens et al. |
| 5,603,221 A | 2/1997 | Maytal |
| 5,628,769 A | 5/1997 | Saringer |
| 5,634,890 A | 6/1997 | Morris |
| 5,634,940 A | 6/1997 | Panyard |
| 5,647,051 A | 7/1997 | Neer |
| 5,647,868 A | 7/1997 | Chinn |
| 5,650,450 A | 7/1997 | Lovette et al. |

(56) References Cited

U.S. PATENT DOCUMENTS

| | | |
|---|---|---|
| 5,651,773 A | 7/1997 | Perry et al. |
| 5,654,279 A | 8/1997 | Rubinsky et al. |
| 5,654,546 A | 8/1997 | Lindsay et al. |
| 5,660,836 A | 8/1997 | Knowlton et al. |
| 5,665,053 A | 9/1997 | Jacobs |
| 5,672,172 A | 9/1997 | Zupkas |
| 5,700,284 A | 12/1997 | Owens et al. |
| 5,725,483 A | 3/1998 | Podolsky |
| 5,733,280 A | 3/1998 | Avitall |
| 5,741,248 A | 4/1998 | Stern et al. |
| 5,746,702 A | 5/1998 | Gelfgat et al. |
| 5,746,736 A | 5/1998 | Tankovich |
| 5,755,663 A | 5/1998 | Larsen et al. |
| 5,755,753 A | 5/1998 | Knowlton et al. |
| 5,755,755 A | 5/1998 | Panyard |
| 5,759,182 A | 6/1998 | Varney et al. |
| 5,759,764 A | 6/1998 | Polovina et al. |
| 5,769,879 A | 6/1998 | Richards et al. |
| 5,785,955 A | 7/1998 | Fischer |
| 5,792,080 A | 8/1998 | Ookawa et al. |
| 5,800,490 A | 9/1998 | Patz et al. |
| 5,814,040 A | 9/1998 | Nelson et al. |
| 5,817,050 A | 10/1998 | Klein et al. |
| 5,817,149 A | 10/1998 | Owens et al. |
| 5,817,150 A | 10/1998 | Owens et al. |
| 5,830,208 A | 11/1998 | Muller et al. |
| 5,833,685 A | 11/1998 | Tortal et al. |
| 5,844,013 A | 12/1998 | Kenndoff et al. |
| 5,853,364 A | 12/1998 | Baker et al. |
| 5,865,841 A | 2/1999 | Kolen et al. |
| 5,871,524 A | 2/1999 | Knowlton |
| 5,871,526 A | 2/1999 | Gibbs et al. |
| 5,885,211 A | 3/1999 | Eppstein et al. |
| 5,891,617 A | 4/1999 | Watson et al. |
| 5,895,418 A | 4/1999 | Saringer |
| 5,901,707 A | 5/1999 | Goncalves |
| 5,902,256 A | 5/1999 | Benaron |
| 5,919,219 A | 7/1999 | Knowlton et al. |
| 5,944,748 A | 8/1999 | Mager et al. |
| 5,948,011 A | 9/1999 | Knowlton et al. |
| 5,954,680 A | 9/1999 | Augustine et al. |
| 5,964,092 A | 10/1999 | Tozuka et al. |
| 5,964,749 A | 10/1999 | Eckhouse et al. |
| 5,967,976 A | 10/1999 | Larsen et al. |
| 5,980,561 A | 11/1999 | Kolen et al. |
| 5,986,167 A | 11/1999 | Arteman et al. |
| 5,989,286 A | 11/1999 | Owens et al. |
| 5,997,530 A | 12/1999 | Nelson et al. |
| 6,017,337 A | 1/2000 | Pira |
| 6,023,932 A | 2/2000 | Johnston |
| 6,032,675 A | 3/2000 | Rubinsky |
| 6,039,694 A | 3/2000 | Larson et al. |
| 6,041,787 A | 3/2000 | Rubinsky |
| 6,047,215 A | 4/2000 | McClure et al. |
| 6,049,927 A | 4/2000 | Thomas et al. |
| 6,051,159 A | 4/2000 | Hao et al. |
| 6,071,239 A | 6/2000 | Cribbs et al. |
| 6,074,415 A | 6/2000 | Der Ovanesian |
| 6,093,230 A | 7/2000 | Johnson et al. |
| 6,102,885 A | 8/2000 | Bass |
| 6,104,952 A | 8/2000 | Tu et al. |
| 6,104,959 A | 8/2000 | Spertell et al. |
| 6,106,517 A | 8/2000 | Zupkas |
| 6,113,558 A | 9/2000 | Rosenschein et al. |
| 6,113,559 A | 9/2000 | Klopotek |
| 6,113,626 A | 9/2000 | Clifton et al. |
| 6,120,519 A | 9/2000 | Weber et al. |
| 6,139,544 A | 10/2000 | Mikus et al. |
| 6,150,148 A | 11/2000 | Nanda et al. |
| 6,151,735 A | 11/2000 | Koby et al. |
| 6,152,952 A | 11/2000 | Owens et al. |
| 6,171,301 B1 | 1/2001 | Nelson et al. |
| 6,180,867 B1 | 1/2001 | Hedengren et al. |
| 6,200,281 B1 | 3/2001 | Frajdenrajch |
| 6,226,996 B1 | 5/2001 | Weber et al. |
| 6,241,753 B1 | 6/2001 | Knowlton |
| 6,264,649 B1 | 7/2001 | Whitcroft et al. |
| 6,273,884 B1 | 8/2001 | Altshuler et al. |
| 6,290,988 B1 | 9/2001 | Van Vilsteren et al. |
| 6,311,090 B1 | 10/2001 | Knowlton |
| 6,311,497 B1 | 11/2001 | Chung |
| 6,312,453 B1 | 11/2001 | Stefanile et al. |
| 6,350,276 B1 | 2/2002 | Knowlton |
| 6,354,297 B1 | 3/2002 | Eiseman |
| 6,357,907 B1 | 3/2002 | Cleveland et al. |
| 6,375,673 B1 | 4/2002 | Clifton et al. |
| 6,377,854 B1 | 4/2002 | Knowlton |
| 6,377,855 B1 | 4/2002 | Knowlton |
| 6,381,497 B1 | 4/2002 | Knowlton |
| 6,381,498 B1 | 4/2002 | Knowlton |
| 6,387,380 B1 | 5/2002 | Knowlton |
| 6,401,722 B1 | 6/2002 | Krag |
| 6,405,090 B1 | 6/2002 | Knowlton |
| 6,413,255 B1 | 7/2002 | Stern |
| 6,425,912 B1 | 7/2002 | Knowlton |
| 6,426,445 B1 | 7/2002 | Young et al. |
| 6,430,446 B1 | 8/2002 | Knowlton |
| 6,430,956 B1 | 8/2002 | Haas et al. |
| 6,438,424 B1 | 8/2002 | Knowlton |
| 6,438,954 B1 | 8/2002 | Goetz et al. |
| 6,438,964 B1 | 8/2002 | Giblin |
| 6,453,202 B1 | 9/2002 | Knowlton |
| 6,458,888 B1 | 10/2002 | Hood et al. |
| 6,461,378 B1 | 10/2002 | Knowlton |
| 6,470,216 B1 | 10/2002 | Knowlton |
| 6,471,693 B1 | 10/2002 | Carroll et al. |
| 6,475,211 B2 | 11/2002 | Chess et al. |
| 6,478,811 B1 | 11/2002 | Dobak, III et al. |
| 6,494,844 B1 | 12/2002 | Van Bladel et al. |
| 6,497,721 B2 | 12/2002 | Ginsburg et al. |
| 6,508,831 B1 | 1/2003 | Kushnir |
| 6,514,244 B2 | 2/2003 | Pope et al. |
| 6,519,964 B2 | 2/2003 | Bieberich |
| 6,523,354 B1 | 2/2003 | Tolbert |
| 6,527,765 B2 | 3/2003 | Kelman et al. |
| 6,527,798 B2 | 3/2003 | Ginsburg et al. |
| 6,544,248 B1 | 4/2003 | Bass |
| 6,547,811 B1 | 4/2003 | Becker et al. |
| 6,548,297 B1 | 4/2003 | Kuri-Harcuch et al. |
| 6,551,255 B2 | 4/2003 | Van Bladel et al. |
| 6,551,341 B2 | 4/2003 | Boylan et al. |
| 6,551,348 B1 | 4/2003 | Blalock et al. |
| 6,551,349 B2 | 4/2003 | Lasheras et al. |
| 6,569,189 B1 | 5/2003 | Augustine et al. |
| 6,585,652 B2 | 7/2003 | Lang et al. |
| 6,592,577 B2 | 7/2003 | Abboud et al. |
| 6,605,080 B1 | 8/2003 | Altshuler et al. |
| 6,607,498 B2 | 8/2003 | Eshel |
| 6,620,187 B2 | 9/2003 | Carson et al. |
| 6,620,188 B1 | 9/2003 | Ginsburg et al. |
| 6,620,189 B1 | 9/2003 | Machold et al. |
| 6,623,430 B1 | 9/2003 | Slayton et al. |
| 6,626,854 B2 | 9/2003 | Friedman et al. |
| 6,632,219 B1 | 10/2003 | Baranov et al. |
| 6,635,053 B1 | 10/2003 | Lalonde et al. |
| 6,643,535 B2 | 11/2003 | Damasco et al. |
| 6,645,162 B2 | 11/2003 | Friedman et al. |
| 6,645,229 B2 | 11/2003 | Matsumura et al. |
| 6,645,232 B2 | 11/2003 | Carson |
| 6,648,904 B2 | 11/2003 | Altshuler et al. |
| 6,656,208 B2 | 12/2003 | Grahn et al. |
| 6,660,027 B2 | 12/2003 | Gruszecki et al. |
| 6,662,054 B2 | 12/2003 | Kreindel et al. |
| 6,682,550 B2 | 1/2004 | Clifton et al. |
| 6,685,731 B2 | 2/2004 | Kushnir et al. |
| 6,694,170 B1 | 2/2004 | Mikus et al. |
| 6,695,874 B2 | 2/2004 | Machold et al. |
| 6,697,670 B2 | 2/2004 | Chornenky |
| 6,699,237 B2 | 3/2004 | Weber et al. |
| 6,699,266 B2 | 3/2004 | Lachenbruch et al. |
| 6,699,267 B2 | 3/2004 | Voorhees et al. |
| 6,718,785 B2 | 4/2004 | Bieberich |
| 6,741,895 B1 | 5/2004 | Gafni et al. |
| 6,743,222 B2 | 6/2004 | Durkin et al. |

(56) References Cited

U.S. PATENT DOCUMENTS

| | | |
|---|---|---|
| 6,746,474 B2 | 6/2004 | Saadat |
| 6,749,624 B2 | 6/2004 | Knowlton |
| 6,764,493 B1 | 7/2004 | Weber et al. |
| 6,764,502 B2 | 7/2004 | Bieberich |
| 6,789,545 B2 | 9/2004 | Littrup et al. |
| 6,795,728 B2 | 9/2004 | Chornenky et al. |
| 6,820,961 B2 | 11/2004 | Johnson |
| 6,821,274 B2 | 11/2004 | McHale et al. |
| 6,840,955 B2 | 1/2005 | Ein |
| 6,849,075 B2 | 2/2005 | Bertolero et al. |
| 6,878,144 B2 | 4/2005 | Altshuler et al. |
| 6,889,090 B2 | 5/2005 | Kreindel |
| 6,892,099 B2 | 5/2005 | Jaafar et al. |
| 6,904,956 B2 | 6/2005 | Noel |
| 6,918,903 B2 | 7/2005 | Bass |
| 6,927,316 B1 | 8/2005 | Faries, Jr. et al. |
| 6,942,022 B2 | 9/2005 | Blangetti et al. |
| 6,945,942 B2 | 9/2005 | Van Bladel et al. |
| 6,948,903 B2 | 9/2005 | Ablabutyan et al. |
| 6,969,399 B2 | 11/2005 | Schock et al. |
| 7,005,558 B1 | 2/2006 | Johansson et al. |
| 7,006,874 B2 | 2/2006 | Knowlton et al. |
| 7,022,121 B2 | 4/2006 | Stern et al. |
| 7,037,326 B2 | 5/2006 | Lee |
| 7,054,685 B2 | 5/2006 | Dimmer et al. |
| 7,060,061 B2 | 6/2006 | Altshuler et al. |
| 7,077,858 B2 | 7/2006 | Fletcher et al. |
| 7,081,111 B2 | 7/2006 | Svaasand et al. |
| 7,083,612 B2 | 8/2006 | Littrup et al. |
| 7,096,204 B1 | 8/2006 | Chen et al. |
| 7,112,712 B1 | 9/2006 | Ancell |
| 7,115,123 B2 | 10/2006 | Knowlton et al. |
| 7,141,049 B2 | 11/2006 | Stern et al. |
| 7,183,360 B2 | 2/2007 | Daniel et al. |
| 7,189,252 B2 | 3/2007 | Krueger |
| 7,192,426 B2 | 3/2007 | Baust et al. |
| 7,204,832 B2 | 4/2007 | Altshuler et al. |
| 7,220,778 B2 | 5/2007 | Anderson et al. |
| 7,229,436 B2 | 6/2007 | Stern et al. |
| 7,258,674 B2 | 8/2007 | Cribbs et al. |
| 7,267,675 B2 | 9/2007 | Stern et al. |
| 7,276,058 B2 | 10/2007 | Altshuler et al. |
| 7,318,821 B2 | 1/2008 | Lalonde et al. |
| 7,331,951 B2 | 2/2008 | Eshel et al. |
| 7,347,855 B2 | 3/2008 | Eshel et al. |
| 7,367,341 B2 | 5/2008 | Anderson et al. |
| 7,532,201 B2 | 5/2009 | Quistgaard et al. |
| 7,572,268 B2 | 8/2009 | Babaev |
| 7,604,632 B2 | 10/2009 | Howlett et al. |
| 7,613,523 B2 | 11/2009 | Eggers et al. |
| 7,615,016 B2 | 11/2009 | Barthe et al. |
| 7,713,266 B2 | 5/2010 | Elkins et al. |
| 7,780,656 B2 | 8/2010 | Tankovich |
| 7,799,018 B2 | 9/2010 | Goulko |
| 7,824,437 B1 | 11/2010 | Saunders |
| 7,828,831 B1 | 11/2010 | Tanhehco et al. |
| 7,850,683 B2 | 12/2010 | Elkins et al. |
| 7,854,754 B2 | 12/2010 | Ting et al. |
| 7,862,558 B2 | 1/2011 | Elkins et al. |
| RE42,277 E | 4/2011 | Jaafar et al. |
| 7,938,824 B2 | 5/2011 | Chornenky et al. |
| 7,959,657 B1 | 6/2011 | Harsy et al. |
| 7,963,959 B2 | 6/2011 | Da Silva et al. |
| 7,967,763 B2 | 6/2011 | Deem et al. |
| 7,993,330 B2 | 8/2011 | Goulko |
| 7,998,137 B2 | 8/2011 | Elkins et al. |
| RE42,835 E | 10/2011 | Chornenky et al. |
| RE43,009 E | 12/2011 | Chornenky et al. |
| 8,133,180 B2 | 3/2012 | Slayton et al. |
| 8,133,191 B2 | 3/2012 | Rosenberg et al. |
| 8,192,474 B2 | 6/2012 | Levinson |
| 8,246,611 B2 | 8/2012 | Paithankar et al. |
| 8,275,442 B2 | 9/2012 | Allison |
| 8,285,390 B2 | 10/2012 | Levinson et al. |
| 8,333,700 B1 | 12/2012 | Barthe et al. |
| 8,337,539 B2 | 12/2012 | Ting et al. |
| 8,366,622 B2 | 2/2013 | Slayton et al. |
| 8,372,130 B2 | 2/2013 | Young et al. |
| 8,397,518 B1 | 3/2013 | Vistakula et al. |
| 8,414,631 B2 | 4/2013 | Quisenberry et al. |
| 8,433,400 B2 | 4/2013 | Prushinskaya et al. |
| 8,506,486 B2 | 8/2013 | Slayton et al. |
| 8,523,775 B2 | 9/2013 | Barthe et al. |
| 8,523,791 B2 | 9/2013 | Castel |
| 8,523,927 B2 | 9/2013 | Levinson et al. |
| 8,535,228 B2 | 9/2013 | Slayton et al. |
| 8,603,073 B2 | 12/2013 | Allison |
| 8,636,665 B2 | 1/2014 | Slayton et al. |
| 8,641,622 B2 | 2/2014 | Barthe et al. |
| 8,663,112 B2 | 3/2014 | Slayton et al. |
| 8,672,848 B2 | 3/2014 | Slayton et al. |
| 8,676,332 B2 | 3/2014 | Fahey |
| 8,690,778 B2 | 4/2014 | Slayton et al. |
| 8,690,779 B2 | 4/2014 | Slayton et al. |
| 8,690,780 B2 | 4/2014 | Slayton et al. |
| 8,702,774 B2 | 4/2014 | Baker et al. |
| 8,758,215 B2 | 6/2014 | Legendre et al. |
| 8,764,693 B1 | 7/2014 | Graham et al. |
| 8,834,547 B2 | 9/2014 | Anderson et al. |
| 2001/0005791 A1 | 6/2001 | Ginsburg et al. |
| 2001/0007952 A1 | 7/2001 | Shimizu |
| 2001/0023364 A1 | 9/2001 | Ahn |
| 2001/0031459 A1 | 10/2001 | Fahy et al. |
| 2001/0039439 A1 | 11/2001 | Elkins et al. |
| 2001/0045104 A1 | 11/2001 | Bailey, Sr. et al. |
| 2001/0047196 A1 | 11/2001 | Ginsburg et al. |
| 2002/0026226 A1 | 2/2002 | Ein |
| 2002/0032473 A1 | 3/2002 | Kushnir et al. |
| 2002/0042607 A1 | 4/2002 | Palmer et al. |
| 2002/0049483 A1 | 4/2002 | Knowlton |
| 2002/0058975 A1 | 5/2002 | Bieberich |
| 2002/0062142 A1 | 5/2002 | Knowlton |
| 2002/0068338 A1 | 6/2002 | Nanda et al. |
| 2002/0082668 A1 | 6/2002 | Ingman |
| 2002/0103520 A1 | 8/2002 | Latham |
| 2002/0107558 A1 | 8/2002 | Clifton et al. |
| 2002/0117293 A1 | 8/2002 | Campbell |
| 2002/0120315 A1 | 8/2002 | Furuno et al. |
| 2002/0128648 A1 | 9/2002 | Weber et al. |
| 2002/0151830 A1 | 10/2002 | Kahn |
| 2002/0151887 A1 | 10/2002 | Stern et al. |
| 2002/0156509 A1 | 10/2002 | Cheung |
| 2002/0188286 A1 | 12/2002 | Quijano et al. |
| 2002/0198518 A1 | 12/2002 | Mikus et al. |
| 2003/0032900 A1 | 2/2003 | Ella |
| 2003/0044764 A1 | 3/2003 | Soane et al. |
| 2003/0055414 A1 | 3/2003 | Altshuler et al. |
| 2003/0062040 A1 | 4/2003 | Lurie et al. |
| 2003/0069618 A1 | 4/2003 | Smith, III et al. |
| 2003/0077326 A1 | 4/2003 | Newton et al. |
| 2003/0077329 A1 | 4/2003 | Kipp et al. |
| 2003/0079488 A1 | 5/2003 | Bieberich |
| 2003/0100936 A1 | 5/2003 | Altshuler et al. |
| 2003/0109908 A1 | 6/2003 | Lachenbruch et al. |
| 2003/0109910 A1 | 6/2003 | Lachenbruch et al. |
| 2003/0109911 A1 | 6/2003 | Lachenbruch et al. |
| 2003/0114885 A1 | 6/2003 | Nova et al. |
| 2003/0120268 A1 | 6/2003 | Bertolero et al. |
| 2003/0125649 A1 | 7/2003 | McIntosh et al. |
| 2003/0187488 A1 | 10/2003 | Kreindel et al. |
| 2003/0199226 A1 | 10/2003 | Sommer et al. |
| 2003/0199859 A1 | 10/2003 | Altshuler et al. |
| 2003/0220594 A1 | 11/2003 | Halvorson et al. |
| 2003/0220635 A1 | 11/2003 | Knowlton et al. |
| 2003/0220674 A1 | 11/2003 | Anderson et al. |
| 2003/0236487 A1 | 12/2003 | Knowlton |
| 2004/0002705 A1 | 1/2004 | Knowlton et al. |
| 2004/0006328 A1 | 1/2004 | Anderson |
| 2004/0009936 A1 | 1/2004 | Tang et al. |
| 2004/0024437 A1 | 2/2004 | Machold et al. |
| 2004/0030332 A1 | 2/2004 | Knowlton et al. |
| 2004/0034341 A1 | 2/2004 | Altshuler et al. |
| 2004/0039312 A1 | 2/2004 | Hillstead et al. |
| 2004/0044384 A1 | 3/2004 | Leber et al. |

(56) References Cited

U.S. PATENT DOCUMENTS

| | | |
|---|---|---|
| 2004/0049178 A1 | 3/2004 | Abboud et al. |
| 2004/0073079 A1 | 4/2004 | Altshuler et al. |
| 2004/0074629 A1 | 4/2004 | Noel |
| 2004/0077977 A1 | 4/2004 | Ella et al. |
| 2004/0082886 A1 | 4/2004 | Timpson |
| 2004/0093042 A1 | 5/2004 | Altshuler et al. |
| 2004/0104012 A1 | 6/2004 | Zhou et al. |
| 2004/0106867 A1 | 6/2004 | Eshel et al. |
| 2004/0133251 A1 | 7/2004 | Altshuler et al. |
| 2004/0162596 A1 | 8/2004 | Altshuler et al. |
| 2004/0176667 A1 | 9/2004 | Mihai et al. |
| 2004/0186535 A1 | 9/2004 | Knowlton |
| 2004/0199226 A1 | 10/2004 | Shadduck |
| 2004/0206365 A1 | 10/2004 | Knowlton |
| 2004/0210214 A1 | 10/2004 | Knowlton |
| 2004/0210287 A1 | 10/2004 | Greene |
| 2004/0215294 A1 | 10/2004 | Littrup et al. |
| 2004/0249427 A1 | 12/2004 | Nabilsi et al. |
| 2004/0259855 A1 | 12/2004 | Anderson et al. |
| 2004/0260209 A1 | 12/2004 | Ella et al. |
| 2004/0260210 A1 | 12/2004 | Ella et al. |
| 2004/0260211 A1 | 12/2004 | Maalouf |
| 2004/0267339 A1 | 12/2004 | Yon et al. |
| 2005/0010197 A1 | 1/2005 | Lau et al. |
| 2005/0033957 A1 | 2/2005 | Enokida |
| 2005/0049526 A1 | 3/2005 | Baer |
| 2005/0049543 A1 | 3/2005 | Anderson et al. |
| 2005/0049661 A1 | 3/2005 | Koffroth |
| 2005/0113725 A1 | 5/2005 | Masuda |
| 2005/0143781 A1 | 6/2005 | Carbunaru et al. |
| 2005/0145372 A1 | 7/2005 | Noel |
| 2005/0149153 A1 | 7/2005 | Nakase et al. |
| 2005/0154314 A1 | 7/2005 | Quistgaard |
| 2005/0154431 A1 | 7/2005 | Quistgaard et al. |
| 2005/0159986 A1 | 7/2005 | Breeland et al. |
| 2005/0177075 A1 | 8/2005 | Meunier et al. |
| 2005/0182462 A1 | 8/2005 | Chornenky et al. |
| 2005/0187495 A1 | 8/2005 | Quistgaard et al. |
| 2005/0187597 A1 | 8/2005 | Vanderschuit |
| 2005/0203446 A1 | 9/2005 | Takashima |
| 2005/0215987 A1 | 9/2005 | Slatkine |
| 2005/0222565 A1 | 10/2005 | Manstein |
| 2005/0251117 A1 | 11/2005 | Anderson et al. |
| 2005/0251120 A1* | 11/2005 | Anderson ............ A61B 5/6804 606/20 |
| 2005/0261753 A1 | 11/2005 | Littrup et al. |
| 2005/0277859 A1 | 12/2005 | Carlsmith et al. |
| 2005/0283144 A1 | 12/2005 | Shiono et al. |
| 2006/0030778 A1 | 2/2006 | Mendlein et al. |
| 2006/0035380 A1 | 2/2006 | Saint-Leger |
| 2006/0036300 A1* | 2/2006 | Kreindel ............... A61B 18/14 607/99 |
| 2006/0041704 A1 | 2/2006 | Choi |
| 2006/0074313 A1 | 4/2006 | Slayton et al. |
| 2006/0079852 A1 | 4/2006 | Bubb et al. |
| 2006/0094988 A1 | 5/2006 | Tosaya et al. |
| 2006/0106836 A1 | 5/2006 | Masugi et al. |
| 2006/0111613 A1 | 5/2006 | Boutillette et al. |
| 2006/0122509 A1 | 6/2006 | Desilets |
| 2006/0189964 A1 | 8/2006 | Anderson et al. |
| 2006/0195168 A1 | 8/2006 | Dunbar et al. |
| 2006/0200063 A1 | 9/2006 | Munro et al. |
| 2006/0206040 A1* | 9/2006 | Greenberg ............ A61H 9/005 601/9 |
| 2006/0206110 A1 | 9/2006 | Knowlton et al. |
| 2006/0211958 A1 | 9/2006 | Rosenberg et al. |
| 2006/0234899 A1 | 10/2006 | Nekmard et al. |
| 2006/0259102 A1* | 11/2006 | Slatkine ............... A61B 17/205 607/88 |
| 2006/0265032 A1 | 11/2006 | Hennings et al. |
| 2006/0270745 A1 | 11/2006 | Hunt et al. |
| 2006/0293734 A1 | 12/2006 | Scott et al. |
| 2007/0010811 A1 | 1/2007 | Stern et al. |
| 2007/0010861 A1 | 1/2007 | Anderson et al. |
| 2007/0032561 A1 | 2/2007 | Lin et al. |
| 2007/0038156 A1 | 2/2007 | Rosenberg |
| 2007/0055156 A1 | 3/2007 | Desilets et al. |
| 2007/0055173 A1 | 3/2007 | DeLonzor et al. |
| 2007/0055179 A1 | 3/2007 | Deem et al. |
| 2007/0055180 A1 | 3/2007 | Deem et al. |
| 2007/0055181 A1 | 3/2007 | Deem et al. |
| 2007/0073367 A1 | 3/2007 | Jones et al. |
| 2007/0078502 A1 | 4/2007 | Weber et al. |
| 2007/0100398 A1 | 5/2007 | Sloan |
| 2007/0106342 A1 | 5/2007 | Schumann |
| 2007/0129714 A1 | 6/2007 | Elkins et al. |
| 2007/0135876 A1 | 6/2007 | Weber |
| 2007/0141265 A1 | 6/2007 | Thomson |
| 2007/0179482 A1* | 8/2007 | Anderson ............ A61B 18/203 606/9 |
| 2007/0198071 A1 | 8/2007 | Ting et al. |
| 2007/0219540 A1 | 9/2007 | Masotti et al. |
| 2007/0239075 A1 | 10/2007 | Rosenberg et al. |
| 2007/0239150 A1 | 10/2007 | Zvuloni et al. |
| 2007/0249519 A1 | 10/2007 | Guha et al. |
| 2007/0255187 A1 | 11/2007 | Branch |
| 2007/0255274 A1 | 11/2007 | Stern et al. |
| 2007/0255362 A1 | 11/2007 | Levinson et al. |
| 2007/0265585 A1 | 11/2007 | Joshi et al. |
| 2007/0265614 A1 | 11/2007 | Stern et al. |
| 2007/0270925 A1 | 11/2007 | Levinson |
| 2007/0282249 A1 | 12/2007 | Quisenberry et al. |
| 2007/0282318 A1 | 12/2007 | Spooner et al. |
| 2008/0014627 A1 | 1/2008 | Merchant et al. |
| 2008/0046047 A1 | 2/2008 | Jacobs |
| 2008/0058784 A1 | 3/2008 | Manstein et al. |
| 2008/0077201 A1 | 3/2008 | Levinson et al. |
| 2008/0077202 A1 | 3/2008 | Levinson |
| 2008/0077211 A1 | 3/2008 | Levinson et al. |
| 2008/0097207 A1 | 4/2008 | Cai et al. |
| 2008/0139901 A1 | 6/2008 | Altshuler et al. |
| 2008/0140061 A1 | 6/2008 | Toubia et al. |
| 2008/0140371 A1 | 6/2008 | Warner |
| 2008/0161892 A1 | 7/2008 | Mercuro et al. |
| 2008/0183164 A1 | 7/2008 | Elkins et al. |
| 2008/0188915 A1 | 8/2008 | Mills et al. |
| 2008/0248554 A1 | 10/2008 | Merchant et al. |
| 2008/0269851 A1 | 10/2008 | Deem et al. |
| 2008/0287839 A1 | 11/2008 | Rosen et al. |
| 2008/0300529 A1 | 12/2008 | Reinstein |
| 2008/0312651 A1 | 12/2008 | Pope et al. |
| 2009/0012434 A1 | 1/2009 | Anderson |
| 2009/0018623 A1 | 1/2009 | Levinson et al. |
| 2009/0018624 A1 | 1/2009 | Levinson et al. |
| 2009/0018625 A1 | 1/2009 | Levinson et al. |
| 2009/0018626 A1 | 1/2009 | Levinson et al. |
| 2009/0018627 A1 | 1/2009 | Levinson et al. |
| 2009/0024023 A1 | 1/2009 | Welches et al. |
| 2009/0076488 A1 | 3/2009 | Welches et al. |
| 2009/0112134 A1 | 4/2009 | Avni |
| 2009/0118722 A1 | 5/2009 | Ebbers et al. |
| 2009/0149929 A1 | 6/2009 | Levinson et al. |
| 2009/0149930 A1 | 6/2009 | Schenck |
| 2009/0171253 A1 | 7/2009 | Davenport |
| 2009/0171334 A1 | 7/2009 | Elkins et al. |
| 2009/0221938 A1 | 9/2009 | Rosenberg et al. |
| 2009/0226424 A1 | 9/2009 | Hsu |
| 2009/0276018 A1 | 11/2009 | Brader |
| 2009/0281464 A1 | 11/2009 | Cioanta et al. |
| 2009/0299234 A1 | 12/2009 | Cho et al. |
| 2009/0306749 A1 | 12/2009 | Mulindwa |
| 2009/0312676 A1 | 12/2009 | Rousso et al. |
| 2009/0312693 A1 | 12/2009 | Thapliyal et al. |
| 2009/0326621 A1 | 12/2009 | El-Galley |
| 2010/0015190 A1 | 1/2010 | Hassler |
| 2010/0028969 A1 | 2/2010 | Mueller et al. |
| 2010/0030306 A1 | 2/2010 | Edelman et al. |
| 2010/0036295 A1 | 2/2010 | Altshuler et al. |
| 2010/0042087 A1 | 2/2010 | Goldboss et al. |
| 2010/0049178 A1 | 2/2010 | Deem et al. |
| 2010/0081971 A1 | 4/2010 | Allison |
| 2010/0087806 A1 | 4/2010 | Da Silva et al. |
| 2010/0152824 A1 | 6/2010 | Allison |
| 2010/0168726 A1 | 7/2010 | Brookman |

(56) References Cited

U.S. PATENT DOCUMENTS

| | | |
|---|---|---|
| 2010/0179531 A1 | 7/2010 | Nebrigic et al. |
| 2010/0198064 A1 | 8/2010 | Perl et al. |
| 2010/0217349 A1 | 8/2010 | Fahey et al. |
| 2010/0241023 A1 | 9/2010 | Gilbert |
| 2010/0268220 A1 | 10/2010 | Johnson et al. |
| 2010/0280582 A1 | 11/2010 | Baker et al. |
| 2011/0009860 A1 | 1/2011 | Chornenky et al. |
| 2011/0040235 A1 | 2/2011 | Castel |
| 2011/0040299 A1 | 2/2011 | Kim et al. |
| 2011/0046523 A1 | 2/2011 | Altshuler et al. |
| 2011/0060323 A1 | 3/2011 | Baust et al. |
| 2011/0066083 A1 | 3/2011 | Tosaya et al. |
| 2011/0066216 A1 | 3/2011 | Ting et al. |
| 2011/0077557 A1 | 3/2011 | Wing et al. |
| 2011/0077723 A1 | 3/2011 | Parish et al. |
| 2011/0112405 A1 | 5/2011 | Barthe et al. |
| 2011/0112520 A1 | 5/2011 | Kreindel |
| 2011/0144631 A1 | 6/2011 | Elkins et al. |
| 2011/0152849 A1 | 6/2011 | Baust et al. |
| 2011/0172651 A1 | 7/2011 | Altshuler et al. |
| 2011/0189129 A1 | 8/2011 | Qiu et al. |
| 2011/0196395 A1 | 8/2011 | Maschke |
| 2011/0196438 A1 | 8/2011 | Mnozil et al. |
| 2011/0202048 A1 | 8/2011 | Nebrigic et al. |
| 2011/0238050 A1 | 9/2011 | Allison et al. |
| 2011/0238051 A1 | 9/2011 | Levinson et al. |
| 2011/0257642 A1 | 10/2011 | Griggs, III |
| 2011/0288537 A1 | 11/2011 | Halaka |
| 2011/0300079 A1 | 12/2011 | Martens et al. |
| 2011/0301585 A1 | 12/2011 | Goulko |
| 2011/0313411 A1 | 12/2011 | Anderson et al. |
| 2011/0313412 A1 | 12/2011 | Kim et al. |
| 2012/0010609 A1 | 1/2012 | Deem et al. |
| 2012/0016239 A1 | 1/2012 | Barthe et al. |
| 2012/0022518 A1 | 1/2012 | Levinson |
| 2012/0022622 A1 | 1/2012 | Johnson et al. |
| 2012/0035475 A1 | 2/2012 | Barthe et al. |
| 2012/0035476 A1 | 2/2012 | Barthe et al. |
| 2012/0046547 A1 | 2/2012 | Barthe et al. |
| 2012/0053458 A1 | 3/2012 | Barthe et al. |
| 2012/0065629 A1 | 3/2012 | Elkins et al. |
| 2012/0083862 A1 | 4/2012 | Altshuler et al. |
| 2012/0101549 A1 | 4/2012 | Schumann |
| 2012/0109041 A1 | 5/2012 | Munz |
| 2012/0158100 A1 | 6/2012 | Schomacker |
| 2012/0209363 A1 | 8/2012 | Williams, III et al. |
| 2012/0233736 A1 | 9/2012 | Tepper et al. |
| 2012/0239123 A1 | 9/2012 | Weber et al. |
| 2012/0253416 A1 | 10/2012 | Erez et al. |
| 2012/0259322 A1 | 10/2012 | Fourkas et al. |
| 2012/0277674 A1 | 11/2012 | Clark, III et al. |
| 2012/0310232 A1 | 12/2012 | Erez |
| 2013/0018236 A1 | 1/2013 | Altshuler et al. |
| 2013/0019374 A1 | 1/2013 | Schwartz |
| 2013/0066309 A1 | 3/2013 | Levinson |
| 2013/0073017 A1 | 3/2013 | Liu et al. |
| 2013/0079684 A1 | 3/2013 | Rosen et al. |
| 2013/0116758 A1 | 5/2013 | Levinson et al. |
| 2013/0116759 A1 | 5/2013 | Levinson et al. |
| 2013/0150844 A1 | 6/2013 | Deem et al. |
| 2013/0158440 A1 | 6/2013 | Allison |
| 2013/0158636 A1 | 6/2013 | Ting et al. |
| 2013/0166003 A1 | 6/2013 | Johnson et al. |
| 2013/0190744 A1 | 7/2013 | Avram et al. |
| 2013/0238062 A1 | 9/2013 | Ron et al. |
| 2013/0245507 A1 | 9/2013 | Khorassani |
| 2013/0253384 A1 | 9/2013 | Anderson et al. |
| 2013/0253493 A1 | 9/2013 | Anderson et al. |
| 2013/0253494 A1 | 9/2013 | Anderson et al. |
| 2013/0253495 A1 | 9/2013 | Anderson et al. |
| 2013/0253496 A1 | 9/2013 | Anderson et al. |
| 2013/0303904 A1 | 11/2013 | Barthe et al. |
| 2013/0303905 A1 | 11/2013 | Barthe et al. |
| 2013/0331914 A1 | 12/2013 | Lee et al. |
| 2014/0005759 A1 | 1/2014 | Fahey et al. |
| 2014/0005760 A1 | 1/2014 | Levinson et al. |
| 2014/0067025 A1 | 3/2014 | Levinson et al. |
| 2014/0142469 A1 | 5/2014 | Britva et al. |
| 2014/0200487 A1 | 7/2014 | Ramdas et al. |
| 2014/0200488 A1 | 7/2014 | Seo et al. |
| 2014/0222121 A1 | 8/2014 | Spence et al. |
| 2014/0277219 A1 | 9/2014 | Nanda |
| 2014/0277302 A1 | 9/2014 | Weber et al. |
| 2014/0277303 A1 | 9/2014 | Biser et al. |
| 2014/0303697 A1 | 10/2014 | Anderson et al. |
| 2015/0209174 A1 | 7/2015 | Abreu |
| 2015/0216719 A1 | 8/2015 | DeBenedictis et al. |
| 2015/0216720 A1 | 8/2015 | DeBenedictis et al. |
| 2015/0216816 A1 | 8/2015 | O'Neil et al. |
| 2015/0223975 A1 | 8/2015 | Anderson et al. |
| 2015/0283022 A1 | 10/2015 | Lee et al. |
| 2015/0328077 A1 | 11/2015 | Levinson |
| 2015/0335468 A1 | 11/2015 | Rose et al. |
| 2015/0342780 A1 | 12/2015 | Levinson et al. |
| 2016/0051308 A1 | 2/2016 | Pennybacker et al. |
| 2016/0051401 A1 | 2/2016 | Yee et al. |
| 2016/0135985 A1 | 5/2016 | Anderson |
| 2016/0324684 A1 | 11/2016 | Levinson et al. |
| 2017/0007309 A1 | 1/2017 | DeBenedictis et al. |
| 2017/0079833 A1 | 3/2017 | Frangineas, Jr. et al. |
| 2017/0105869 A1 | 4/2017 | Frangineas, Jr. et al. |
| 2017/0165105 A1 | 6/2017 | Anderson et al. |
| 2017/0196731 A1 | 7/2017 | DeBenedictis et al. |
| 2017/0239079 A1 | 8/2017 | Root et al. |
| 2017/0325992 A1 | 11/2017 | DeBenedictis et al. |
| 2017/0325993 A1 | 11/2017 | Jimenez Lozano et al. |
| 2017/0326042 A1 | 11/2017 | Zeng et al. |
| 2017/0326346 A1 | 11/2017 | Jimenez Lozano et al. |
| 2018/0185081 A1 | 7/2018 | O'Neil et al. |
| 2018/0185189 A1 | 7/2018 | Weber et al. |
| 2018/0263677 A1 | 9/2018 | Hilton et al. |
| 2018/0271767 A1 | 9/2018 | Jimenez Lozano et al. |
| 2018/0310950 A1 | 11/2018 | Yee et al. |

FOREIGN PATENT DOCUMENTS

| | | |
|---|---|---|
| CA | 2585214 A1 | 10/2007 |
| CH | 333982 A | 11/1958 |
| CN | 86200604 U | 10/1987 |
| CN | 2514795 Y | 10/2002 |
| CN | 2514811 Y | 10/2002 |
| CN | 1511503 A | 7/2004 |
| CN | 1741777 A | 3/2006 |
| CN | 1817990 A | 8/2006 |
| CN | 2843367 Y | 12/2006 |
| CN | 2850584 Y | 12/2006 |
| CN | 2850585 Y | 12/2006 |
| CN | 200970265 Y | 11/2007 |
| CN | 101259329 A | 9/2008 |
| CN | 101309657 A | 11/2008 |
| DE | 532976 C | 9/1931 |
| DE | 2851602 A1 | 6/1980 |
| DE | 3622808 A1 | 1/1987 |
| DE | 4213584 A1 | 11/1992 |
| DE | 4224595 A1 | 1/1994 |
| DE | 4238291 A1 | 5/1994 |
| DE | 4445627 A1 | 6/1996 |
| DE | 19800416 A1 | 7/1999 |
| EP | 263069 A2 | 4/1988 |
| EP | 0397043 A1 | 11/1990 |
| EP | 0406244 A1 | 1/1991 |
| EP | 560309 A1 | 9/1993 |
| EP | 0598824 A1 | 6/1994 |
| EP | 1030611 A1 | 8/2000 |
| EP | 1201266 A1 | 5/2002 |
| EP | 1568395 A1 | 8/2005 |
| EP | 1627662 A1 | 2/2006 |
| EP | 2260801 A2 | 12/2010 |
| EP | 2289598 A1 | 3/2011 |
| EP | 2527005 A1 | 11/2012 |
| EP | 1991315 B1 | 11/2013 |
| ES | 2010938 A6 | 12/1989 |
| FR | 854937 A | 4/1940 |
| FR | 2744358 A1 | 8/1997 |

(56) References Cited

FOREIGN PATENT DOCUMENTS

| | | |
|---|---|---|
| FR | 2745935 A1 | 9/1997 |
| FR | 2767476 A1 | 2/1999 |
| FR | 2776920 A1 | 10/1999 |
| FR | 2789893 A1 | 8/2000 |
| FR | 2792828 A1 | 11/2000 |
| FR | 2805989 A1 | 9/2001 |
| FR | 2844996 A1 | 4/2004 |
| GB | 387960 A | 2/1933 |
| GB | 1417989 A | 12/1975 |
| GB | 2120944 A | 12/1983 |
| GB | 2202447 A | 9/1988 |
| GB | 2248183 A | 4/1992 |
| GB | 2263872 A | 8/1993 |
| GB | 2286660 A | 8/1995 |
| GB | 2323659 A | 9/1998 |
| JP | 58187454 A | 11/1983 |
| JP | S6094113 A | 5/1985 |
| JP | S6094113 U | 6/1985 |
| JP | 62082977 A | 4/1987 |
| JP | 63076895 A | 4/1988 |
| JP | 01223961 A | 9/1989 |
| JP | 03051964 A | 3/1991 |
| JP | 03259975 A | 11/1991 |
| JP | 04093597 A | 3/1992 |
| JP | 06261933 A | 9/1994 |
| JP | 07194666 A | 8/1995 |
| JP | 07268274 A | 10/1995 |
| JP | 09164163 A | 6/1997 |
| JP | 10216169 A | 8/1998 |
| JP | 10223961 A | 8/1998 |
| JP | 2000503154 A | 3/2000 |
| JP | 3065657 B2 | 7/2000 |
| JP | 2001046416 A | 2/2001 |
| JP | 2002125993 A | 5/2002 |
| JP | 2002224051 A | 8/2002 |
| JP | 2002282295 A | 10/2002 |
| JP | 2002290397 A | 10/2002 |
| JP | 2002543668 A | 12/2002 |
| JP | 2003190201 A | 7/2003 |
| JP | 2004013600 A | 1/2004 |
| JP | 2004073812 A | 3/2004 |
| JP | 2004159666 A | 6/2004 |
| JP | 2005039790 A | 2/2005 |
| JP | 2005065984 A | 3/2005 |
| JP | 2005110755 A | 4/2005 |
| JP | 2005509977 A | 4/2005 |
| JP | 3655820 B2 | 6/2005 |
| JP | 2005520608 A | 7/2005 |
| JP | 2005237908 A | 9/2005 |
| JP | 2005296042 A | 10/2005 |
| JP | 2005323716 A | 11/2005 |
| JP | 2006026001 A | 2/2006 |
| JP | 2006094988 A | 4/2006 |
| JP | 2006130055 A | 5/2006 |
| JP | 2006520949 A | 9/2006 |
| JP | 2007270459 A | 10/2007 |
| JP | 2008532591 A | 8/2008 |
| JP | 2009515232 A | 4/2009 |
| JP | 2009189757 A | 8/2009 |
| KR | 200173222 Y1 | 12/1999 |
| KR | 1020040094508 A | 11/2004 |
| KR | 102006134245 A | 12/2006 |
| KR | 20090000258 U | 1/2009 |
| KR | 1020130043299 A | 4/2013 |
| KR | 1020140038165 A | 3/2014 |
| RU | 2036667 C1 | 6/1995 |
| SU | 532976 A1 | 11/1978 |
| TW | 0476644 B | 2/2002 |
| WO | 8503216 A1 | 8/1985 |
| WO | 9114417 A1 | 10/1991 |
| WO | 9404116 A1 | 3/1994 |
| WO | 9509596 A1 | 4/1995 |
| WO | 9623447 A1 | 8/1996 |
| WO | 9626693 A1 | 9/1996 |
| WO | 9636293 A1 | 11/1996 |
| WO | 9637158 A1 | 11/1996 |
| WO | 9704832 A1 | 2/1997 |
| WO | 9705828 A1 | 2/1997 |
| WO | 9722262 A2 | 6/1997 |
| WO | 9724088 A1 | 7/1997 |
| WO | 9725798 A1 | 7/1997 |
| WO | 9748440 A1 | 12/1997 |
| WO | 1998002123 A1 | 1/1998 |
| WO | 9829134 A2 | 7/1998 |
| WO | 9831321 A1 | 7/1998 |
| WO | 9841156 A1 | 9/1998 |
| WO | 9841157 A1 | 9/1998 |
| WO | 9909928 A1 | 3/1999 |
| WO | 9916502 A1 | 4/1999 |
| WO | 9938469 A1 | 8/1999 |
| WO | 9949937 A1 | 10/1999 |
| WO | 0044346 A1 | 8/2000 |
| WO | 0044349 A1 | 8/2000 |
| WO | 0065770 A1 | 11/2000 |
| WO | 0067685 A1 | 11/2000 |
| WO | 0100269 A1 | 1/2001 |
| WO | 0113989 A1 | 3/2001 |
| WO | 0114012 A1 | 3/2001 |
| WO | 0134048 A1 | 5/2001 |
| WO | 0205736 A1 | 1/2002 |
| WO | 02102921 A1 | 12/2002 |
| WO | 03007859 A1 | 1/2003 |
| WO | 03013334 A2 | 2/2003 |
| WO | 03078596 A2 | 9/2003 |
| WO | 03079916 A1 | 10/2003 |
| WO | 2004000098 A2 | 12/2003 |
| WO | 2004080279 A2 | 9/2004 |
| WO | 2004090939 A2 | 10/2004 |
| WO | 2005033957 A1 | 4/2005 |
| WO | 2005046540 A1 | 5/2005 |
| WO | 2005060354 A2 | 7/2005 |
| WO | 2005096979 A1 | 10/2005 |
| WO | 2005112807 A2 | 12/2005 |
| WO | 2005112815 A1 | 12/2005 |
| WO | 2006066226 A1 | 6/2006 |
| WO | 2006094348 A1 | 9/2006 |
| WO | 2006106836 A1 | 10/2006 |
| WO | 2006116603 A2 | 11/2006 |
| WO | 2006122136 A1 | 11/2006 |
| WO | 2006127467 A2 | 11/2006 |
| WO | 2007012083 A2 | 1/2007 |
| WO | 2007028975 A1 | 3/2007 |
| WO | 2007041642 A2 | 4/2007 |
| WO | 2007093998 A1 | 8/2007 |
| WO | 2007101039 A1 | 9/2007 |
| WO | 2007127924 A2 | 11/2007 |
| WO | 2007145421 A1 | 12/2007 |
| WO | 2007145422 A1 | 12/2007 |
| WO | 2008006018 A2 | 1/2008 |
| WO | 2008039556 A1 | 4/2008 |
| WO | 2008039557 A1 | 4/2008 |
| WO | 2008055243 A2 | 5/2008 |
| WO | 2008094485 A2 | 8/2008 |
| WO | 2008143678 A1 | 11/2008 |
| WO | 2009011708 A1 | 1/2009 |
| WO | 2009026471 A1 | 2/2009 |
| WO | 2010077841 A1 | 7/2010 |
| WO | 2010127315 A2 | 11/2010 |
| WO | 2012012296 A1 | 1/2012 |
| WO | 2012103242 A1 | 8/2012 |
| WO | 2013013059 A1 | 1/2013 |
| WO | 2013075006 A1 | 5/2013 |
| WO | 2013075016 A1 | 5/2013 |
| WO | 2013190337 A1 | 12/2013 |
| WO | 2014151872 A3 | 9/2014 |
| WO | 2014191263 A1 | 12/2014 |
| WO | 2015117001 A1 | 8/2015 |
| WO | 2015117005 A1 | 8/2015 |
| WO | 2015117026 A2 | 8/2015 |
| WO | 2015117032 A1 | 8/2015 |
| WO | 2015117036 A2 | 8/2015 |
| WO | 2016028796 A1 | 2/2016 |
| WO | 2016048721 A1 | 3/2016 |

(56) References Cited

FOREIGN PATENT DOCUMENTS

OTHER PUBLICATIONS

Aguilar et al., "Modeling Cryogenic Spray Temperature and Evaporation Rate Based on Single-Droplet Analysis," Eighth International Conference on Liquid Atomization and Spray Systems, Pasadena, CA, USA, Jul. 2000, 7 pages.
Al-Sakere, B. et al. "Tumor Ablation with Irreversible Electroporation," PLoS One, Issue 11, Nov. 2007, 8 pages.
Alster, T. et al., "Cellulite Treatment Using a Novel Combination Radiofrequency, Infrared Light, and Mechanical Tissue Manipulation Device," Journal of Cosmetic and Laser Therapy, vol. 7, 2005, pp. 81-85.
Ardevol, A. et al., "Cooling Rates of Tissue Samples During Freezing with Liquid Nitrogen," Journal of Biochemical and Biophysical Methods, vol. 27, 1993, pp. 77-86.
Arena, C. B. et al., "High-Frequency Irreversible Electroporation (H-FIRE) for Non-Thermal Ablation Without Muscle Contraction," BioMedical Engineering OnLine 2011, 10:102, Nov. 21, 2011, 21 pgs.
Becker, S. M. et al. "Local Temperature Rises Influence In Vivo Electroporation Pore Development: A Numerical Stratum Corneum Lipid Phase Transition Model," Journal of Biomechanical Engineering, vol. 129, Oct. 2007, pp. 712-721.
Bohm, T. et al., "Saline-Enhanced Radiofrequency Ablation of Breast Tissue: an in Vitro Feasibility Study," Investigative Radiology, vol. 35 (3), 2000, pp. 149-157.
Bondei, E. et al., "Disorders of Subcutaneous Tissue (Cold Panniculitis)," Dermatology in General Medicine, Fourth Edition, vol. 1, Chapter 108, 1993, Section 16, pp. 1333-1334.
Burge, S.M. et al., "Hair Follicle Destruction and Regeneration in Guinea Pig Skin after Cutaneous Freeze Injury," Cryobiology, 27(2), 1990, pp. 153-163.
Coban, Y. K. et al., "Ischemia-Reperfusion Injury of Adipofascial Tissue: An Experimental Study Evaluating Early Histologic and Biochemical Alterations in Rats," Mediators of Inflammation, 2005, 5, pp. 304-308.
Del Pino, M. E. et al. "Effect of Controlled Volumetric Tissue Heating with Radiofrequency on Cellulite and the Subcutaneous Tissue of the Buttocks and Thighs," Journal of Drugs in Dermatology, vol. 5, Issue 8, Sep. 2006, pp. 714-722.
Donski, P. K. et al., "The Effects of Cooling no Experimental Free Flap Survival," British Journal of Plastic Surgery, vol. 33, 1980, pp. 353-360.
Duck, F. A., Physical Properties of Tissue, Academic Press Ltd., chapters 4 & 5, 1990, pp. 73-165.
Duncan, W. C. et al., "Cold Panniculitis," Archives of Dermatology, vol. 94, Issue 6, Dec. 1966, pp. 722-724.
Epstein, E. H. et al., "Popsicle Panniculitis," The New England Journal of Medicine, 282(17), Apr. 23, 1970, pp. 966-967.
Final Office Action; U.S. Appl. No. 11/750,953; dated Jul. 5, 2012, 11 pages.
Fournier, L. et al. "Lattice Model for the Kinetics of Rupture of Fluid Bilayer Membranes," Physical Review, vol. 67, 2003, pp. 051908-1-051908-11.
Gabriel, S. et al., "The Dielectric Properties of Biological Tissues: II. Measurements in the Frequency Range 10 Hz to 20 GHz," Physics in Medicine and Biology, vol. 41, 1996, pp. 2251-2269.
Gage, A. "Current Progress in Cryosurgery," Cryobiology 25, 1988, pp. 483-486.
Gatto, H. "Effects of Thermal Shocks on Interleukin-1 Levels and Heat Shock Protein 72 (HSP72) Expression in Normal Human Keratinocytes," PubMed, Archives of Dermatological Research, vol. 284, Issue 7, 1992: pp. 414-417 [Abstract].
Hale, H. B. et al., "Influence of Chronic Heat Exposure and Prolonged Food Deprivation on Excretion of Magnesium, Phosphorus, Calcium, Hydrogen Ion & Ketones," Aerospace Medicine, vol. 39—No. 9, Sep. 1968, pp. 919-926.
Heller Page, E. et al., "Temperature-dependent skin disorders," Journal of the American Academy of Dermatology, vol. 18, No. 5, Pt 1, May 1988, pp. 1003-1019.
Hemmingsson, A. et al. "Attenuation in Human Muscle and Fat Tissue in Vivo and in Vitro," Acra Radiologica Diagnosis, vol. 23, No. 2, 1982, pp. 149-151.
Henry, F. et al., "Les Dermatoses Hivernales," Rev Med Liege, 54:11, 1999, pp. 864-866. [Abstract Attached].
Hernan, P. et al., "Study for the evaluation of the efficacy of Lipocryolysis (EEEL)", Nov. 30, 2011.
Hernan, R. P., "A Study to Evaluate the Action of Lipocryolysis", 33(3) CryoLellers, 2012, pp. 176-180.
Holland, DB. et al. "Cold shock induces the synthesis of stress proteins in human keratinocytes," PubMed Journal of Investigative Dermatology; 101(2): Aug. 1993, pp. 196-199.
Holman, W. L. et al., "Variation in Cryolesion Penetration Due to Probe Size and Tissue Thermal Conductivity," The Annals of Thoracic Surgery, vol. 53, 1992, pp. 123-126.
Hong, J.S. et al., "Patterns of Ice Formation in Normal and Malignant Breast Tissue," Cryobiology 31, 1994, pp. 109-120.
Huang et al. "Comparative Proteomic Profiling of Murine Skin," Journal of Investigative Dermatology, vol. 121(1), Jul. 2003, pp. 51-64.
Jalian, H. R. et al., "Cryolipolysis: A Historical Perspective and Current Clinical Practice", 32(1) Semin. Cutan. Med. Surg., 2013, pp. 31-34.
Levchenko et al., "Effect of Dehydration on Lipid Metabolism" Ukrainskii Biokhimicheskii Zhurnal, vol. 50, Issue 1, 1978, pp. 95-97.
L'Vova, S.P. "Lipid Levels and Lipid Peroxidation in Frog Tissues During Hypothermia and Hibernation" Ukrainskii Biokhimicheskii Zhurnal, vol. 62, Issue 1, 1990, pp. 65-70.
Zelickson, B. et al., "Cryolipolysis for Noninvasive Fat Cell Destruction: Initial Results from a Pig Model", 35 Dermatol. Sug., 2009, pp. 1-9.
Notice of Opposition to European Patent No. EP2162083; Date of Opposition Aug. 31, 2016; 70 pages.
Notice of Opposition to European Patent No. EP2162083; Date of Opposition Sep. 22, 2016; 70 pages.
Vuraki et al.; A device for cryovacuum treatment; Med tech, Jan.-Feb. 1989, (1):46-9 (extracted from PUBMED on Jun. 29, 2016).
Vuraki et al., A device for cryovacuum treatment; Military Medical Academy im. Korov, Leningrad; Feb. 8, 1988; 7 pages.
International Search Report and Written Opinion for PCT/US2007/069694; Applicant: Juniper Medical, Inc.; dated Nov. 23, 2007, 12 pages.
Isambert, H. "Understanding the Electroporation of Cells and Artificial Bilayer Membranes," Physical Review Letters, vol. 80, No. 15, 1998, pp. 3404-3707.
Kellum, R. E. et al., "Sclerema Neonatorum: Report of Case and Analysis of Subcutaneous and Epidermal-Dermal Lipids by Chromatographic Methods," Archives of Dermatology, vol. 97, Apr. 1968, pp. 372-380.
Koska, J. et al., "Endocrine Regulation of Subcutaneous Fat Metabolism During Cold Exposure in Humans," Annals of the New York Academy of Sciences, vol. 967, 2002,pp. 500-505.
Kundu, S. K. et al., "Breath Acetone Analyzer: Diagnostic Tool to Monitor Dietary Fat Loss," Clinical Chemistry, vol. 39, Issue (1), 1993, pp. 87-92.
Kundu, S. K. et al., "Novel Solid-Phase Assay of Ketone Bodies in Urine," Clinical Chemistry, vol. 37, Issue (9), 1991, pp. 1565-1569.
Kuroda, S. et al. "Thermal Distribution of Radio-Frequency Inductive Hyperthermia Using an Inductive Aperture-Type Applicator: Evaluation of the Effect of Tumor Size and Depth", Medical and Biological Engineering and Computing, vol. 37, 1999, pp. 285-290.
Laugier, P. et al., "In Vivo Results with a New Device for Ultrasonic Monitoring of Pig Skin Cryosurgery: The Echographic Cryprobe," The Society for Investigative Dermatology, Inc., vol. 111, No. 2, Aug. 1998, pp. 314-319.
Lidagoster, MD et al., "Comparison of Autologous Fat Transfer in Fresh, Refrigerated, and Frozen Specimens: An Animal Model," Annals of Plastic Surgery, vol. 44, No. 5, May 2000, pp. 512-515.

(56) References Cited

OTHER PUBLICATIONS

Liu, A. Y.-C. et al., "Transient Cold Shock Induces the Heat Shock Response upon Recovery at 37 C in Human Cells," Journal of Biological Chemistry, , 269(20), May 20, 1994, pp. 14768-14775.

Maize, J.C. "Panniculitis," Cutaneous Pathology, Chapter 13, 1998, 327-344.

Malcolm, G. T. et al., "Fatty Acid Composition of Adipose Tissue in Humans: Differences between Subcutaneous Sites," The American Journal of Clinical Nutrition, vol. 50, 1989, pp. 288-291.

Manstein, D. et al. "A Novel Cryotherapy Method of Non-invasive, Selective Lipolysis," LasersSurg.Med 40:S20, 2008, p. 104.

Manstein, D. et al. "Selective Cryolysis: A Novel Method of Non-Invasive Fat Removal," Lasers in Surgery and Medicine: The Official Journal of the ASLMS, vol. 40, No. 9, Nov. 2008, pp. 595-604.

Mayoral, "Case Reports: Skin Tightening with a Combined Unipolar and Bipolar Radiofrequency Device," Journal of Drugs in Dermatology, 2007, pp. 212-215.

Mazur, P. "Cryobiology: the Freezing of Biological Systems," Science, 68, 1970, pp. 939-949.

Merrill, T. "A Chill to the Heart: A System to Deliver Local Hypothermia Could One Day Improve the Lives of Heart-Attack Patients," Mechanical Engineering Magazine, Oct. 2010, 10 pages.

Miklavcic, D. et al. "Electroporation-Based Technologies and Treatments," The Journal of Membrane Biology (2010) 236:1-2, 2 pgs.

Moschella, S. L. et al., "Diseases of the Subcutaneous Tissue," in Dermatology, Second Edition, vol. 2, 1985 Chapter 19, Section II (W.B. Saunders Company, 1980) pp. 1169-1181.

Murphy, J. V. et al., "Frostbite: Pathogenesis and Treatment" The Journal of Trauma: Injury, Infection, and Critical Care, vol. 48, No. 1, Jan. 2000, pp. 171-178.

Nagao, T. et al., "Dietary Diacylglycerol Suppresses Accumulation of Body Fat Compared to Triacylglycerol in Men a Double-Blind Controlled Trial," The Journal of Nutrition, vol. 130, Issue (4), 2000, pp. 792-797.

Nagle, W. A. et al. "Cultured Chinese Hamster Cells Undergo Apoptosis After Exposure to Cold but Nonfreezing Temperatures," Cryobiology 27, 1990, pp. 439-451.

Nagore, E. et al., "Lipoatrophia Semicircularis—a Traumatic Panniculitis: Report of Seven Cases and Review of the Literature," Journal of the American Academy of Dermatology, vol. 39, Nov. 1998, pp. 879-881.

Nanda, G.S. et al., "Studies on electroporation of thermally and chemically treated human erythrocytes," Bioelectrochemistry and Bioenergetics, 34, 1994, pp. 129-134, 6 pgs.

Narins, D.J. et al. "Non-Surgical Radiofrequency Facelift", The Journal of Drugs in Dermatology, vol. 2, Issue 5, 2003, pp. 495-500.

Nielsen, B. "Thermoregulation in Rest and Exercise," Acta Physiologica Scandinavica Supplementum, vol. 323 (Copenhagen 1969), pp. 7-74.

Nishikawa, H. et al. "Ultrastructural Changes and Lipid Peroxidation in Rat Adipomusculocutaneous Flap Isotransplants after Normothermic Storage and Reperfusion," Transplantation, vol. 54, No. 5,1992, pp. 795-801.

Nurnberger, F. "So-Called Cellulite: An Invented Disease," Journal of Dermatologic Surgery and Oncology, Mar. 1978, pp. 221-229.

Pease, G. R. et al., "An Integrated Probe for Magnetic Resonance Imaging Monitored Skin Cryosurgery," Journal of Biomedical Engineering, vol. 117, Feb. 1995, pp. 59-63.

Pech, P. et al., "Attenuation Values, Volume Changes and Artifacts in Tissue Due to Freezing," Acta Radiologica ,vol. 28, Issue 6, 1987, pp. 779-782.

Peterson, L. J. et al., "Bilateral Fat Necrosis of the Scrotum," Journal of Urology, vol. 116, 1976, pp. 825-826.

Phinney, S. D. et al., "Human Subcutaneous Adipose Tissue Shows Site-Specific Differences in Fatty Acid Composition," The American Journal of Clinical Nutrition, vol. 60, 1994, pp. 725-729.

Pierard, G.E. et al., "Cellulite: From Standing Fat Herniation to Hypodermal Stretch Marks," The American Journal of Dermatology, vol. 22, Issue 1, 2000, pp. 34-37, [Abstract].

Pope, K. et al. "Selective Fibrous Septae Heating: An Additional Mechanism of Action for Capacitively Coupled Monopolar Radiofrequency" Thermage, Inc. Article, Feb. 2005, 6pgs.

Quinn, P. J. "A Lipid-Phase Separation Model of Low-Temperature Damage to Biological Membranes," Cryobiology, 22, 1985, 128-146.

Rabi, T. et al., "Metabolic Adaptations in Brown Adipose Tissue of the Hamster in Extreme Ambient Temperatures," American Journal of Physiology, vol. 231, Issue 1, Jul. 1976, pp. 153-160.

Renold, A.E. et al. "Adipose Tissue" in Handbook of Physiology, Chapter 15, (Washington, D.C., 1965) pp. 169-176.

Rossi, A. B. R. et al. "Cellulite: a Review," European Academy of Dermatology and Venercology, 2000, pp. 251-262, 12 pgs.

Rubinsky, B. "Principles of Low Temperature Cell Preservation," Heart Failure Reviews, vol. 8, 2003, pp. 277-284.

Rubinsky, B. et al., "Cryosurgery: Advances in the Application of low Temperatures to Medicine," International Journal of Refrigeration, vol. 14, Jul. 1991, pp. 190-199.

Saleh, K.Y. et al., "Two-Dimensional Ultrasound Phased Array Design for Tissue Ablation for Treatment of Benign Prostatic Hyperplasia," International Journal of Hyperthermia, vol. 20, No. 1, Feb. 2004, pp. 7-31.

Schoning, P. et al., "Experimental Frostbite: Freezing Times, Rewarming Times, and Lowest Temperatures of Pig Skin Exposed to Chilled Air," Cryobiology 27, 1990, pp. 189-193.

Shephard, R. J. "Adaptation to Exercise in the Cold," Sports Medicine, vol. 2, 1985, pp. 59-71.

Sigma-Aldrich "Poly(ethylene glycol) and Poly(ethylene oxide)," http://www.sigmaaldrich.com/materials-science/materialscience-;products.htmi?TablePage=2020411 0, accessed Oct. 19, 2012.

Smalls, L. K. et al. "Quantitative Model of Cellulite: Three Dimensional Skin Surface Topography, Biophysical Characterization, and Relationship to Human Perception," International Journal of Cosmetic Science, vol. 27, Issue 5, Oct. 2005, 17 pgs.

Thermage, News Release, "Study Published in Facial Plastic Surgery Journal Finds Selective Heating of Fibrous Septae Key to Success and Safety of Thermage ThermaCool System," Jun. 20, 2005, 2 pages.

Vallerand, A.L. "Cold Stress Increases Lipolysis, FFA RA and TG/FFA Cycling in Humans," Aviation, Space, and Environmental Medicine 70(1), 1999, pp. 42-50.

Wang, X. et al., "Cryopreservation of Cell/Hydrogel Constructs Based on a new Cell-Assembling Technique," Sep. 5, 2009, 40 pages.

Wharton, D. A. et al., "Cold Acclimation and Cryoprotectants in a Freeze-Tolerant Antarctic Nematode, Panagrolaimus Davidi,", Journal of Comparative Physiology, vol. 170, No. 4, Mar. 2000, 2 pages.

Winkler, C. et al., "Gene Transfer in Laboratory Fish: Model Organisms for the Analysis of Gene Function," in Transgenic Animals, Generation and Use (The Netherlands 1997), pp. 387-395.

Young, H. E. et al. "Isolation of Embryonic Chick Myosatellite and Pluripotent Stem Cells" The Journal of Tissue Culture Methods, vol. 14, Issue 2, 1992, pp. 85-92.

Zouboulis, C. C. et al., "Current Developments and Uses of Cryosurgery in the Treatment of Keloids and Hypertrophic Scars," Wound Repair and Regeneration, vol. 10, No. 2, 2002, pp. 98-102.

\* cited by examiner

TREATMENT APPARATUS FOR REMOVING HEAT FROM SUBCUTANEOUS LIPID-RICH CELLS AND MASSAGING TISSUE

CROSS-REFERENCE TO RELATED APPLICATIONS

The present application is a continuation of U.S. patent application Ser. No. 13/616,633, filed Sep. 14, 2012, now abandoned, which is a continuation of U.S. patent application Ser. No. 11/750,953, filed on May 18, 2007, now abandoned. These applications are incorporated by reference in their entireties.

TECHNICAL FIELD

The present application relates generally to treatment devices, systems, and methods for removing heat from subcutaneous lipid-rich cells; more particularly, but not exclusively, several embodiments are directed toward a treatment device including an actuator such as a vibration device, a pneumatic device and/or a massage device and at least one treatment unit to affect subcutaneous lipid-rich cells.

BACKGROUND

Excess body fat, or adipose tissue, can detract from personal appearance and athletic performance. Excess adipose tissue may be present in various locations of the body, including, for example, the thigh, buttocks, abdomen, knees, back, face, arms, and other areas. Moreover, excess adipose tissue is thought to magnify the unattractive appearance of cellulite, which forms when subcutaneous fat protrudes into the dermis and creates dimples where the skin is attached to underlying structural fibrous strands. Cellulite and excessive amounts of adipose tissue are often considered to be unappealing. Moreover, significant health risks may be associated with higher amounts of excess body fat. An effective way of controlling or removing excess body fat therefore is needed.

Liposuction is a method for selectively removing adipose tissue to "sculpt" a person's body. Liposuction typically is performed by plastic surgeons or dermatologists using specialized surgical equipment that invasively removes subcutaneous adipose tissue via suction. One drawback of liposuction is that it is a surgical procedure, and the recovery may be painful and lengthy. Moreover, the procedure typically requires the injection of tumescent anesthetics, which is often associated with temporary bruising. Liposuction can also have serious and occasionally even fatal complications. In addition, the cost for liposuction is usually substantial. Other emerging techniques for removal of subcutaneous adipose tissue include mesotherapy, laser-assisted liposuction, and high intensity focused ultrasound.

Conventional non-invasive treatments for removing excess body fat typically include topical agents, weight-loss drugs, regular exercise, dieting, or a combination of these treatments. One drawback of these treatments is that they may not be effective or even possible under certain circumstances. For example, when a person is physically injured or ill, regular exercise may not be an option. Similarly, weight-loss drugs or topical agents are not an option when they cause an allergic or negative reaction. Furthermore, fat loss in selective areas of a person's body cannot be achieved using general or systemic weight-loss methods.

Other non-invasive treatment methods include applying heat to a zone of subcutaneous lipid-rich cells. U.S. Pat. No. 5,948,011 discloses altering subcutaneous body fat and/or collagen by heating the subcutaneous fat layer with radiant energy while cooling the surface of the skin. The applied heat denatures fibrous septae made of collagen tissue and may destroy fat cells below the skin, and the cooling protects the epidermis from thermal damage. This method is less invasive than liposuction, but it still may cause thermal damage to adjacent tissue, and can also be painful and unpredictable.

Additional methods of reducing subcutaneous adipocytes cool or otherwise selectively remove or target them, as disclosed for example in U.S. Patent Publication Nos. 2003/0220674 and 2005/0251120, the entire disclosures of which are incorporated herein. These publications disclose, among other things, the concept of reducing the temperature of subcutaneous adipocytes to selectively affect them without damaging the cells in the epidermis and other surrounding tissue. Although the methods and devices disclosed in these publications are promising, several improvements for enhancing the implementation of these methods and devices would be desirable.

BRIEF DESCRIPTION OF THE DRAWINGS

In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn are not intended to convey any information regarding the actual shape of the particular elements, and have been solely selected for ease of recognition in the drawings.

FIG. 4b is an isometric and exploded view of the treatment device of FIG. 4a.

DETAILED DESCRIPTION

A. Overview

Figure 1:
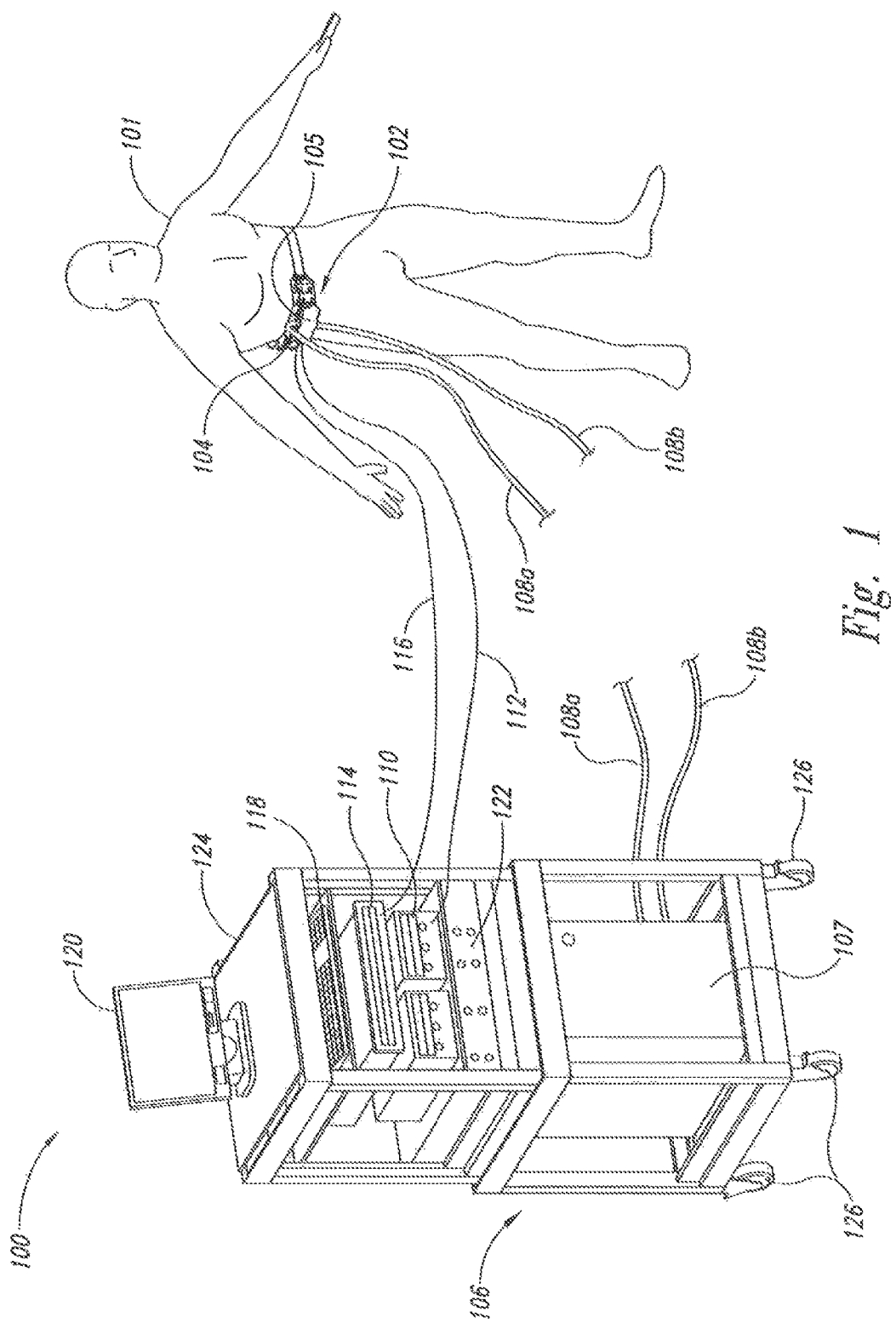
FIG. 1 is an isometric view of a system for removing heat from subcutaneous lipid-rich cells in accordance with an embodiment of the invention.

This document describes devices, systems, and methods for cooling subcutaneous adipose tissue. The term "subcutaneous tissue" means tissue lying beneath the dermis and includes subcutaneous fat, or adipose tissue, which primarily is composed of lipid-rich cells, or adipocytes. Several of the details set forth below are provided to describe the following embodiments and methods in a manner sufficient to enable a person skilled in the relevant art to practice, make and use them. Several of the details and advantages described below, however, may not be necessary to practice certain embodiments and methods of the invention. Additionally, the invention may include other embodiments and methods that are within the scope of the claims but are not described in detail.

Reference throughout this specification to "one embodiment" or "an embodiment" means that a particular feature, structure, or characteristic described in connection with the embodiment is included in at least one embodiment of the present invention. Thus, the occurrences of the phrases "in one embodiment" or "in an embodiment" in various places throughout this specification are not necessarily all referring to the same embodiment. Furthermore, the particular features, structures, or characteristics may be combined in any suitable manner in one or more embodiments. The headings provided herein are for convenience only and do not limit or interpret the scope or meaning of the claimed invention.

The present invention is directed toward a treatment device for removing heat from subcutaneous lipid-rich cells of a subject and methods for using such a device. The treatment device includes an actuator that provides mechanical energy to the tissue. The mechanical energy provided may include a vibratory component that can range between low and ultra-high frequencies, and such energy may include various combinations of two or more frequencies tailored to produce the desired effect on the subcutaneous tissue. According to an embodiment, for example, disruption of adipose tissue cooled by an external treatment device may be enhanced by vibrating the cooled tissue. As applied to the tissue, then, such vibration may impart a vibratory effect, a massage effect, a pulsatile effect, combinations thereof, etc.

Several embodiments of treatment devices for removing heat from subcutaneous lipid-rich cells include at least one actuator and a treatment unit. The actuator may connect directly to the treatment unit, or the actuator may be affixed to a housing for the treatment unit. Alternatively, the treatment device may further include a flexible substrate containing a treatment unit and the actuator is connected to the flexible substrate. The actuator may provide mechanical energy to the tissue. This may be done in a number of different ways; for example, varying mechanical energy, such as vibratory energy, may be imparted through the applicator. Alternatively, or additionally the tissue may be directly manipulated with varying pneumatic pressure. The actuator may include a motor with an eccentric weight or other vibratory motors such as hydraulic motors, electric motors, solenoids, other mechanical motors, or piezoelectric shakers to provide the energy to the treatment site. The treatment units may use a number of cooling technologies including, for example, thermoelectric coolers, recirculating chilled fluid, vapor compression elements, or phase change cryogenic devices. One skilled in the art will recognize that there are a number of other cooling technologies and mechanical movement technologies that could be used such that the treatment units and mechanical devices need not be limited to those described herein.

Another embodiment of a treatment device may include one or more actuators coupled to at least one of a plurality of interconnected hinged or coupled segments; the hinged or coupled segments allow the treatment device to conform to a body portion. The one or more actuators may rigidly be affixed or releasably coupled to any portion of the interconnected hinged or coupled segment. Alternatively, the one or more actuators may be on or embedded in a flexible substrate which further contains the treatment units.

In yet another embodiment, a treatment device comprises one or more actuators controllable to provide varying intensity, frequency, location and/or duration of motion during treatment. The motion profile can, for example, be configured to provide motion along a selected region of the treatment device for a pre-selected or controlled time period. Alternatively, the motion profile may, for example, be configured to provide periods of increased intensity. In other embodiments, the motion profile may vary over time to provide a decreasing or an increasing intensity during treatment according to a predetermined pattern. In still other embodiments, different actuators may simultaneously provide different types of motion or motion of varying intensity, frequency, location and/or duration between or among the actuators, or some actuators may be deactivated while others are activated in varying patterns throughout the course of treatment.

Additional embodiments disclosed below are directed toward methods of affecting lipid-rich cells by applying a treatment device and imparting mechanical energy to the target cells from one or more actuators. The actuator may provide mechanical energy imparted to the tissue. Depending on the frequency and amplitude of the mechanical energy, the mechanical energy may yield an effect such as a vibratory effect, a massage effect, a pulsatile effect, or any combination thereof that sends mechanical energy to the patient via or in connection with the treatment device. One embodiment of such a method includes arranging a treatment device in a desired configuration, cooling a heat exchanging surface of a treatment unit to a desired temperature, placing the cooled heat exchanging surface proximate to the subject's skin, activating an actuator that imparts mechanical energy to the tissue, and reducing the temperature of a region such that lipid-rich cells in the region are affected while non-lipid-rich cells in the region generally are not affected. Alternatively, the actuator and the treatment units may be on and/or within a flexible substrate.

Further embodiments disclosed below are directed toward systems for efficiently removing heat from subcutaneous lipid-rich cells. An embodiment of a system includes a treatment device having one or more actuators coupled to a hinge, frame, substrate or other portion of the treatment device. The actuator is configured to impart mechanical motion relative to the skin of a patient, including positive and negative pressure; for example, the actuator may include a pneumatic feature, such as vacuum, for drawing and/or pressuring the subject's tissue away from and/or towards, respectively, the treatment device. In another embodiment, the actuator may include a vibratory device for providing mechanical vibration transferred to the subject's tissue via the treatment device. In yet another embodiment, the actuator may provide mechanical energy to produce a massage effect, thus providing mechanical massage to the treated region. When placed proximate to a subject's skin, the treatment device is capable of reducing a temperature of a region such that lipid-rich cells in the region are affected while non-lipid-rich cells in the epidermis and/or dermis are not generally affected.

B. System for More Effectively Selectively Reducing Lipid-Rich Cells

FIG. 1 is an isometric view of an embodiment of a treatment system 100 for removing heat from subcutaneous lipid-rich cells of a subject 101. The system 100 may include a treatment device 104 including an actuator 105. The treatment device 104 may be placed, for example, at an abdominal area 102 of the subject 101 or another suitable area for cooling or removing heat from the subcutaneous lipid-rich cells of the subject 101. Various embodiments of the treatment device 104 are described in more detail below with reference to FIGS. 2-12.

The system 100 may further include a treatment unit 106 and supply and return fluid lines 108a-b between the treatment device 104 and the fluid source 107. The fluid source 107 can remove heat from a coolant to a heat sink and provide a chilled coolant to the treatment device 104 via the fluid lines 108a-b. Examples of the circulating coolant include water, glycol, synthetic heat transfer fluid, oil, a refrigerant, and/or any other suitable heat-conducting fluid. The fluid lines 108a-b may be hoses or other conduits constructed from polyethylene, polyvinyl chloride, polyurethane, and/or other materials that can accommodate the particular circulating coolant. The treatment unit 106 may be a refrigeration unit, a cooling tower, a thermoelectric chiller, or any other device capable of removing heat from a coolant. Alternatively, a municipal water supply (i.e., tap water) may be used in place of the treatment unit.

As explained in more detail below, the treatment device 104 includes at least one actuator 105 and at least one treatment unit. The treatment unit may be a Peltier-type thermoelectric element, and the treatment device 104 may have a plurality of individually controlled treatment units to create a custom spatial cooling profile and/or a time-varying cooling profile. The system 100 may further include a power supply 110 and a processing unit 114 operatively coupled to the treatment device 104 and the actuator 105. In one embodiment, the power supply 110 provides a direct current voltage to a thermoelectric treatment device 104 and/or the actuator 105 to remove heat from the subject 101. The processing unit 114 may monitor process parameters via sensors (not shown) placed proximate to the treatment device 104 through power line 116 to, among other things, adjust the heat removal rate based on the process parameters. The processing unit 114 may further monitor process parameters to adjust actuator 105 based on the process parameters. The processing unit 114 may be in direct electrical communication with treatment device 104 through electrical line 112 as shown in FIG. 1; alternatively, processing unit 114 may be connected to treatment device (and/or any number of other components of system 100 as discussed below) via a wireless or an optical communication link. Processing unit 114 may be any processor, Programmable Logic Controller, Distributed Control System, and the like. Note that power line 116 and line 112 are shown in FIG. 1 without any support structure. Alternatively, power line 116 and line 112 (and other lines including, but not limited to fluid lines 108a-b) may be bundled into or otherwise accompanied by a conduit or the like to protect such lines, enhance user safety and ergonomic comfort, ensure unwanted motion (and thus potential inefficient removal of heat from subject 101) is minimized, and to provide an aesthetic appearance to system 100. Examples of such a conduit include a flexible polymeric, fabric, or composite sheath, an adjustable arm, etc. Such a conduit may be designed (via adjustable joints, etc.) to "set" the conduit in place for the treatment of subject 101.

In another aspect, the processing unit 114 may be in electrical or other communication with an input device 118, an output device 120, and/or a control panel 122. The input device 118 may be a keyboard, a mouse, a touch screen, a push button, a switch, a potentiometer, any combination thereof, and any other device or devices suitable for accepting user input. The output device 120 may be include a display screen, a printer, a medium reader, an audio device, any combination thereof, and any other device or devices suitable for providing user feedback. The control panel 122 may include visual indicator devices or controls (lights, numerical displays, etc.) and/or audio indicator devices or controls. In alternative embodiments, the control panel 122 may be contained in, attached to, or integrated with the treatment device 104. In the embodiment shown in FIG. 1, processing unit 114, power supply 110, control panel 122, treatment unit 106, input device 118, and output device 120 are carried by a rack or cart 124 with wheels 126 for portability. In alternative embodiments, the processing unit 114 may be contained in, attached to, or integrated with the treatment device 104 and/or the actuator 105. In yet another embodiment, the various components may be fixedly installed at a treatment site.

C. Actuator for Use with a Treatment Device

Figure 2:
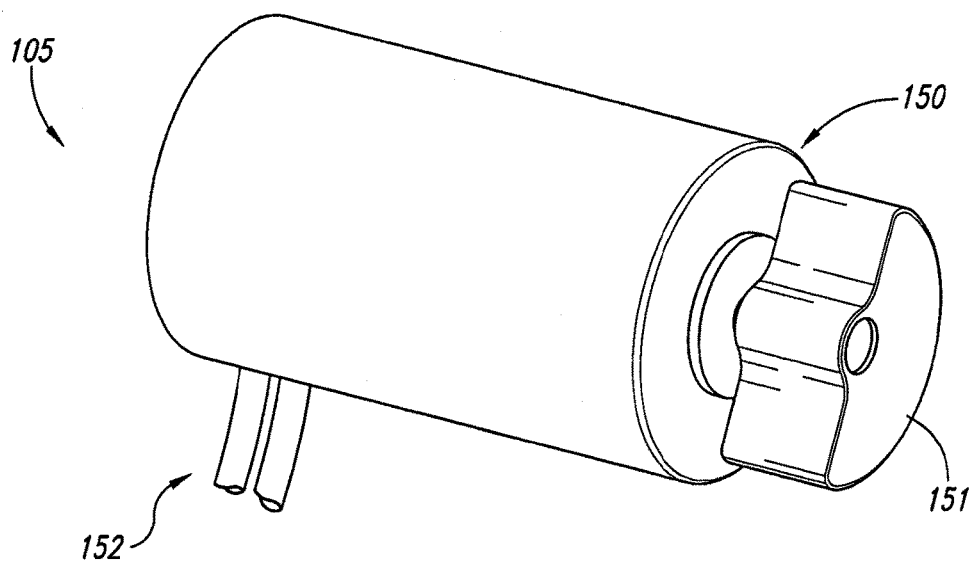
FIG. 2 is an isometric view of an actuator for use with a treatment device in accordance with an embodiment of the invention.
Figure 3:
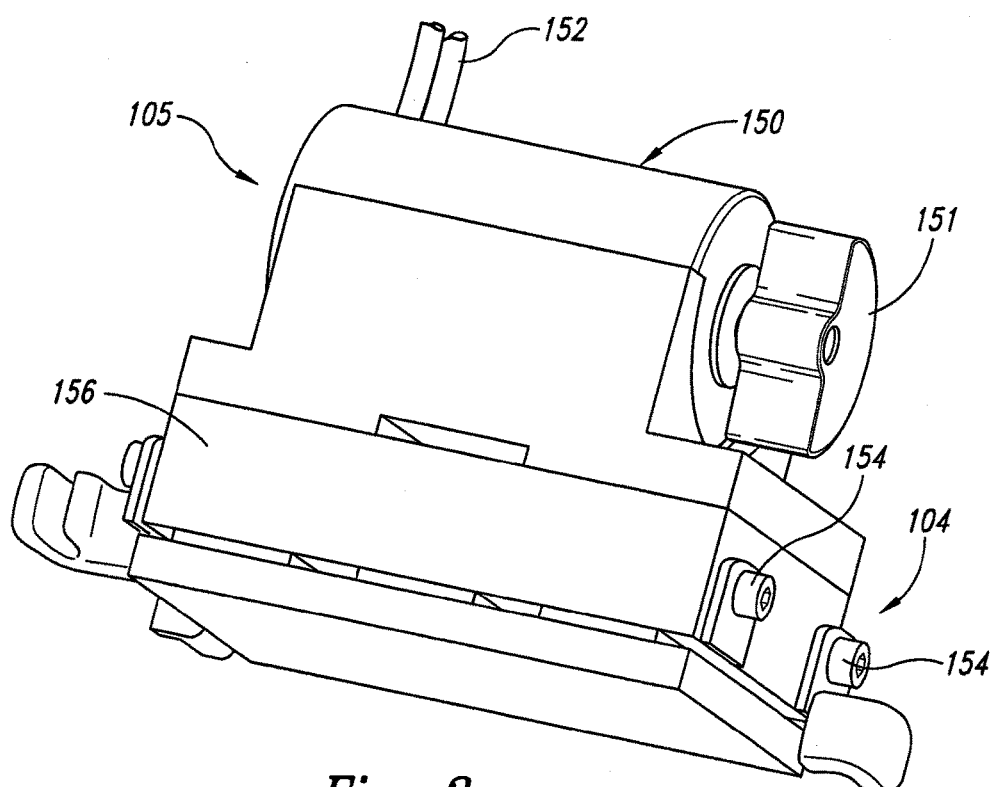
FIG. 3 is an isometric view of the actuator of FIG. 2 coupled to a frame segment of a treatment device in accordance with an embodiment of the invention.

FIGS. 2, 3 and 4 are isometric views of embodiments of actuators 105 for use with a treatment device 104 suitable for use in the system 100. The actuator may provide mechanical energy to create a vibratory, massage, and/or pulsatile effect. The actuator may include one or more various motors, for example, motors with eccentric weight, or other vibratory motors such as hydraulic motors, electric motors, pneumatic motors, solenoids, other mechanical motors, piezoelectric shakers, etc. to provide vibratory energy to the treatment site. Further embodiments include a plurality of actuators 105 for use in connection with a single treatment device 104 in any desired combination. For example, an eccentric weight actuator may be associated with one treatment device 104 while a pneumatic motor may be associated with another section of the same treatment device. This, for example, would give the operator of treatment system 100 options for differential treatment of lipid rich cells within a single region or among multiple regions of subject 101. The use of one or more actuators and actuator types in various combinations and configurations with treatment device 104 is possible with all the embodiments of the invention.

D. Treatment Device Having an Actuator Such as a Vibratory Device

FIG. 2 shows an actuator 105 including a motor 150 containing an eccentric weight 151 to create mechanical vibration, pulsing and/or cycling effect. Power is supplied to the motor 150 through power lines 152. Alternatively, the motor 150 could be battery powered or could include an electrical plug. Alternatively, vibration, pulsing and/or cycling can be induced by a mechanism using hydraulic, electric, electromechanical, solenoid, or mechanical devices as are known in the art. FIG. 3 shows the motor 150 of FIG. 2 affixed to a selected portion of the treatment device 104 as described further herein.

According to one embodiment, an actuator 105 is affixed by screws 154 or other mechanical fixation devices to a housing 156 of the treatment device 104 to transmit mechanical energy through the treatment device 104 to the tissue of a patient. Alternatively, the actuator 105 may be strapped in place proximate to the treatment device 104 to transmit mechanical energy through the treatment device 104 of the tissue of the patient. According to still further embodiments, the actuator 105 may be incorporated into the treatment device 104 to provide an integrated treatment device with an activator for providing mechanical energy.

According to alternative embodiments, the treatment device 104 includes a plurality of links that are mechanically coupled with a plurality of hinges and a single actuator to transfer mechanical vibratory energy through adjacent links to the skin. Alternately, the actuator can be incorporated into more than one link, or a plurality of actuators may be used with a single treatment device.

In specific embodiments of the motor 150, the eccentric weight may be a weight machined out of brass; alternatively, the mass may be fabricated from steel, aluminum, alloys thereof, high density polymeric materials, or any other relatively dense material. According to further embodiments, the motor used is a brushed DC motor; alternatively, any electric motor could be used, or any other means of rotating the mass as is known in the art.

The actuator 105 need not have a rotating eccentric weight; rather, other embodiments may have an electrical coil or the like to create a varying or pulsing energy. The electrical coil, for example, may include a solenoid, a vibrating armature or a voice coil. According to an embodiment using a solenoid, a coil is energized to create a magnetic field that moves a steel or iron armature. The armature may be attached to a mass and can be driven into a hard stop to produce a pulse. If the hard stop is mechanically coupled to the device applied to the skin, this energy will be transferred into the tissue. This method of imparting mechanical energy to lipid-rich cells so to create a massage or massage-like effect is suited, but not necessarily limited, to lower frequencies and higher impulse energies.

A specific embodiment of a vibrating armature or voice coil has a coil driven by an alternating current to move or oscillate the armature back and forth. The inertia of this motion may be transferred through the link into the tissue to provide an actuator for enhancing the vibratory effect on the lipid-rich cells.

According to still further embodiments, the mechanical force may create a massage massage-like effect using a water hammer. Water, or any of a number of other heat transfer fluids suitable for cooling the thermoelectric coolers, can have significant mass, and when flowing through tubing, these fluids can commensurately have significant momentum. By quickly halting the flow of such a fluid, such as, e.g., by placing a solenoid valve in the fluid line and closing the flow path, a properly designed system transfers the momentum of the fluid to the treatment device 104 and into the tissue. According to aspects of this embodiment, such a water hammer or similar momentum-transferring arrangement is suited to low frequencies. Further, such an arrangement may reduce the heat transfer rate, which may be desirable for certain applications.

In operation, the motor 150 shown in FIG. 2 rotates an eccentric weight to provide mechanical energy. The motor is rigidly attached to the treatment device 104, for example, to a housing 156 of the treatment device 104 as shown in FIG. 3. Mechanical energy creating a pulsing, cycling, or oscillation effect is applied by the centripetal force generated as the eccentric weight rotates, creating a varying or pulsing mechanical energy. This energy is transferred through the treatment device 104 to the patient's skin and underlying tissue. The frequency of the vibration can be increased by increasing the rotational rate of the weight. A higher frequency also increases the applied force of the vibration. According to one embodiment, the frequency of massage (or vibration) is in the range of about 0.1 Hz to about 50 MHz, and more preferably in the range of between about 200 Hz and about 400 Hz, according to alternative embodiments; the frequency of massage (or vibration) can be higher or lower. The motor 150 may further include passive or active damping materials (not shown). The force applied during each rotation of the weight may be increased, for example, by increasing the mass of the weight or increasing the distance between the center of gravity of the weight and its axis of rotation. Similarly, decreasing the mass of the weight or decreasing the distance between the center of gravity of the weight and its axis of rotation may, for example, decrease the force applied during each rotation of the weight. The appropriate force is dependent on the mass of the housing 156 or other component of the treatment device 104 to which the motor 150 is applied. According to embodiments, a more massive housing assembly requires a more massive eccentric weight so that the vibratory force is transferred through the housing 156 into the tissue to which the treatment device 104 is applied.

The illustrated embodiment of the actuator as shown in FIG. 2 can allow a compact and relatively low power actuator 105 to be coupled to one or more of the link assemblies of a treatment device 104. By coupling the actuator 105 to the treatment device 104, mechanical energy may be applied at any time in the cooling or heating process without necessarily removing the applicator. Alternatively, the applicator may be removed and an actuator such as a commercial massage device may be applied to the tissue or the tissue may be manually massaged.

In addition, the illustrated embodiment may provide acceleration and enhancement of the ischemic reperfusion damage to adipose tissue through mechanical massage or vibration. Further, the illustrated embodiment of the actuator and the treatment device combine to provide an enhanced ability to disrupt crystallized adipose cells and further affect lipid-rich cells.

E. Treatment Device Having an Actuator Such as a Vacuum Device

Figure 4A:
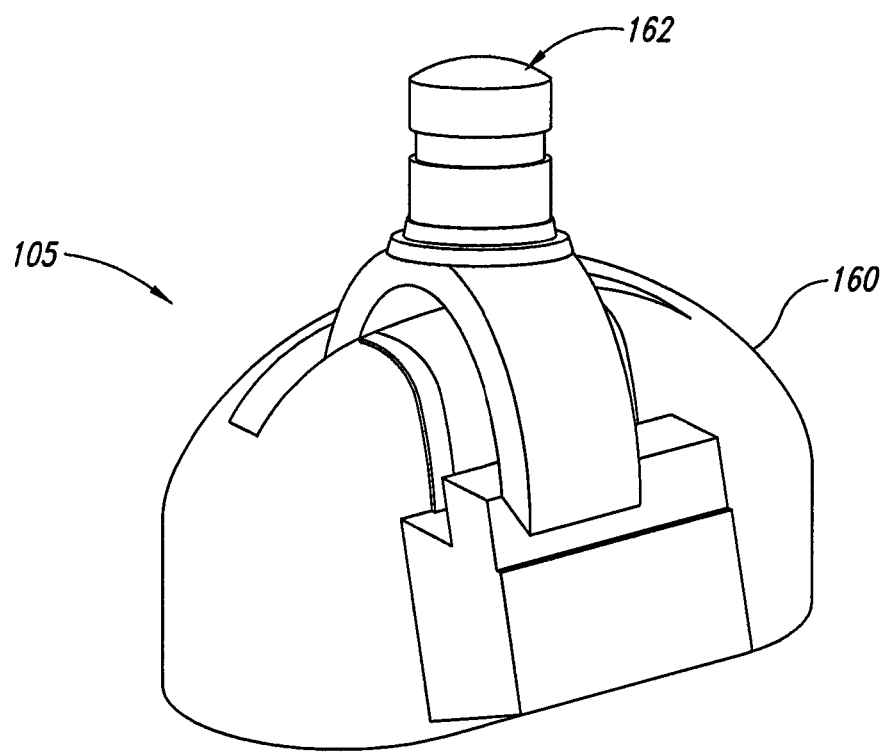
FIG. 4a is an isometric view of an actuator for use with a treatment device in accordance with an embodiment of the invention.
Figure 4B:
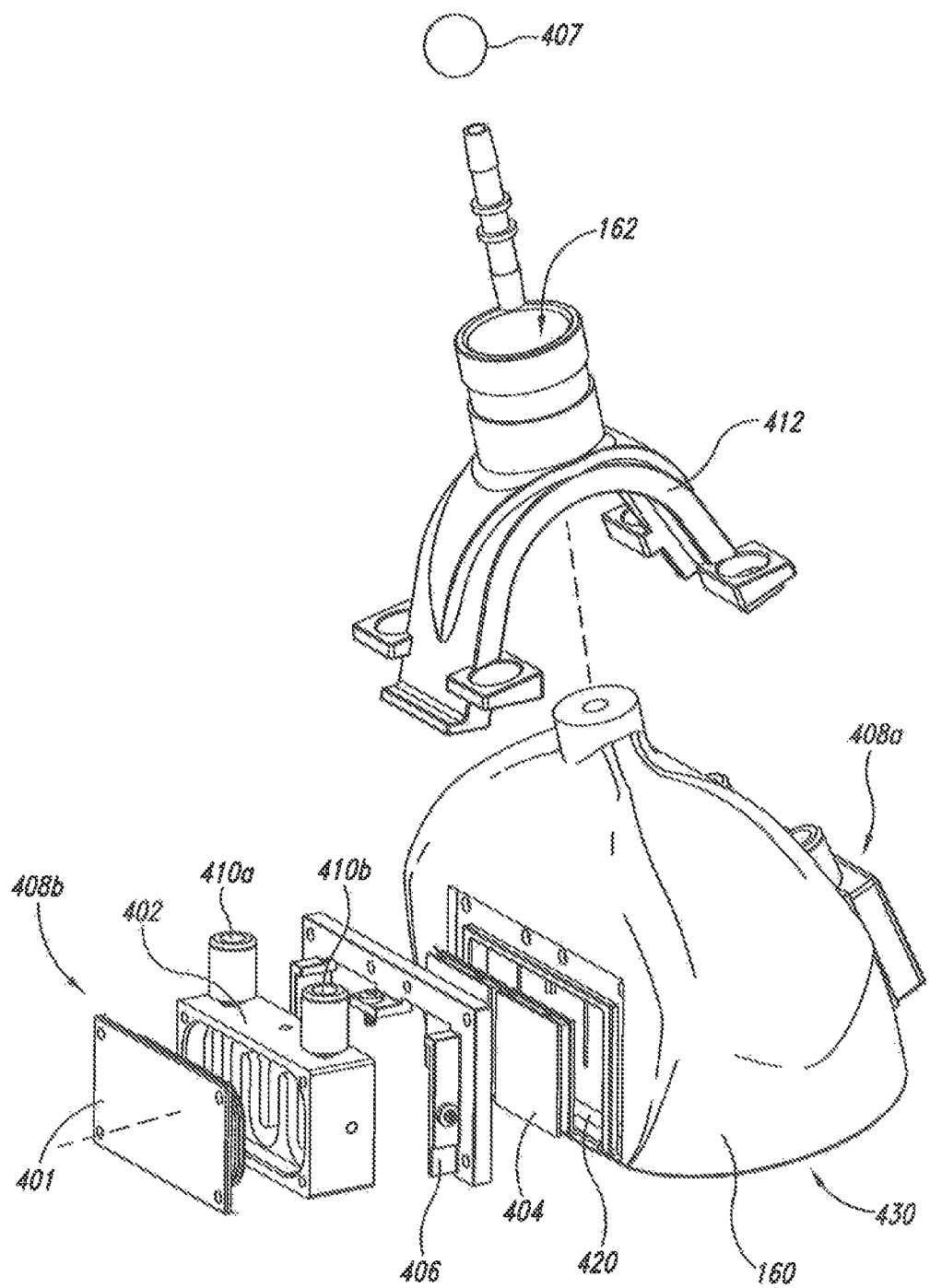
Figure 5:
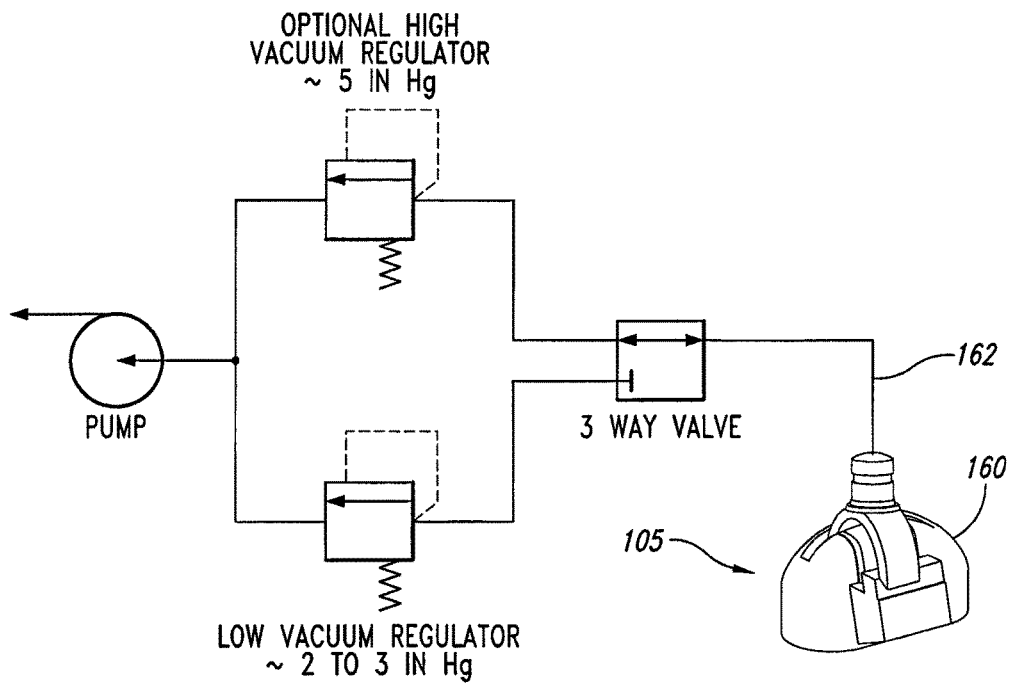
FIG. 5 is a schematic view of an embodiment of the actuator of FIG. 4 in accordance with an embodiment of the invention.
Figure 6:
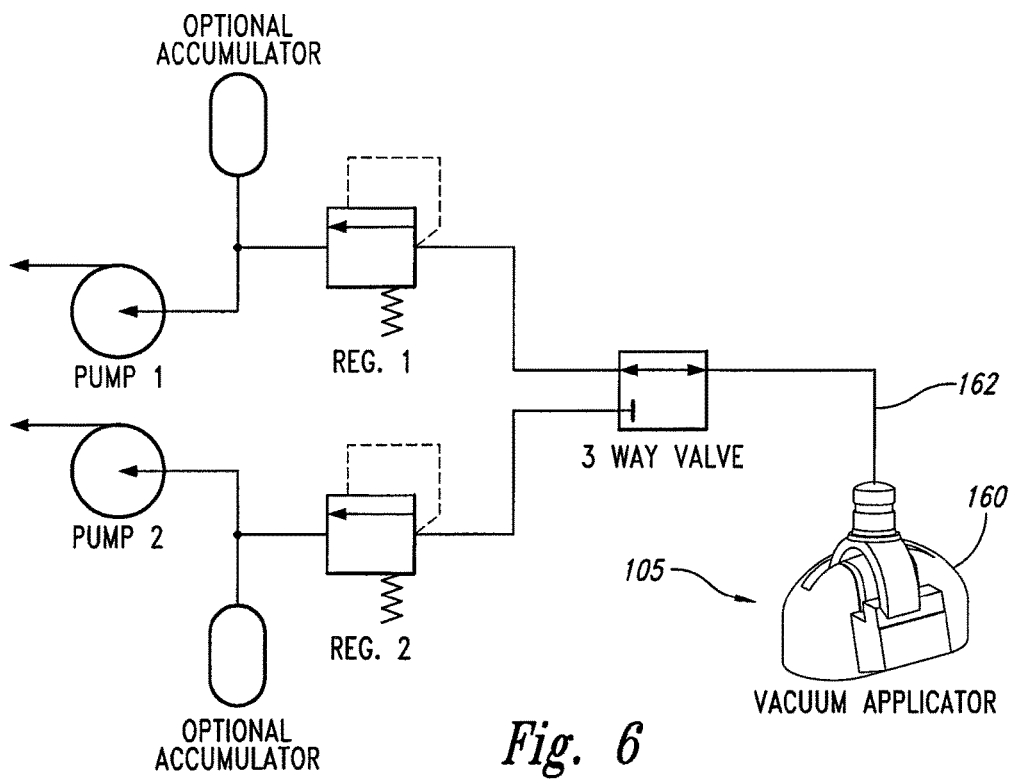
FIG. 6 is a schematic view of an embodiment of the actuator of FIG. 4 in accordance with an alternative embodiment of the invention.
Figure 7:
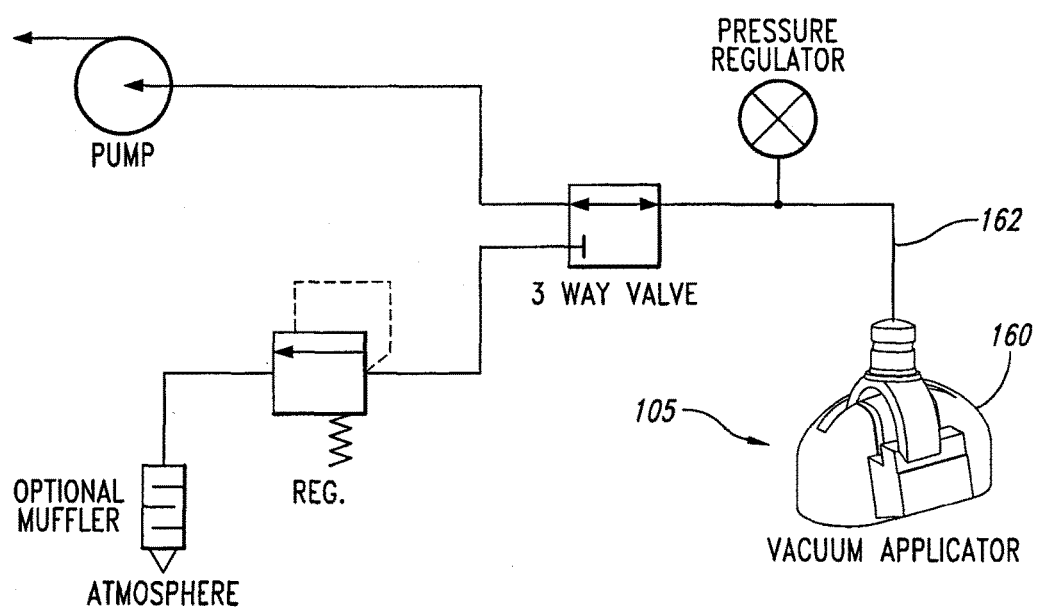
FIG. 7 is a schematic view of an embodiment of the actuator of FIG. 4 in accordance with an alternative embodiment of the invention.

FIGS. 4a and 4b show a vacuum device 160 suitable for use with a treatment device for applying a vacuum to the subject's tissue before, during and/or after cooling. As discussed with reference to FIG. 3, the actuator 105, shown as a vacuum device 160 in this embodiment, may include a vacuum cup and treatment units 408a, 408b affixed to the vacuum device 160. The vacuum device 160 may provide mechanical energy to a treatment region. Imparting mechanical vibratory energy to the patient's tissue by repeatedly applying and releasing a vacuum to the subject's tissue, for instance, creates a massage action. Alternatively, massage devices as are known in the art may be used to enhance the desired effect on lipid-rich cells. FIGS. 5-7 illustrate schematic diagrams of embodiments of the vacuum device 160.

As described herein, techniques for incorporating massage into a treatment device 105 may include using a pressure differential to draw the skin against a thermally controlled plate or plates. In an actuator such as the vacuum device 160 shown in FIGS. 4a and 4b, a vacuum line 162 can be connected to the vacuum device 160. In operation, air is evacuated from a chamber in the vacuum device 160 create a pressure differential which draws a fold of the subject's skin and subcutaneous tissue up inside a reservoir 430 of the vacuum device 160 and against the treatment units 408a, 408b.

The vacuum device 160 defines the reservoir 430 for receiving tissue of a subject during treatment. The vacuum device 160 may further include treatment units 408a, 408b positioned at opposite sides of the vacuum device 160. Alternatively, the treatment units 408a, 408b may be adjacent one another. Further, vacuum device 160 may comprise a vacuum cup and a single treatment unit or more than two treatment units. As shown in the example of FIG. 4b, one or both of the treatment units 408a, 408b may include a heat exchanging interface 420 for transferring heat to/from the subject 101. A cryoprotectant or coupling agent (not shown) may be applied to the heat exchanging interface 420 to prevent ice from forming thereon when the temperature is reduced to a temperature around or below the freezing point of water (0° C.). In one embodiment, the heat exchanging interface 420 is generally planar, but in other embodiments, the heat exchanging interface 420 is non-planar (e.g., curved, faceted, etc.) The interface 420 may be constructed from any suitable material with a thermal conductivity greater than 0.05 Watts/Meter K, and in many embodiments, the thermal conductivity is more than 0.1 Watts/Meter K. Examples of suitable materials include aluminum, other metals, metal alloys, graphite, ceramics, some polymeric materials, composites, or fluids contained in a flexible membrane. Portions of the heat exchanging element 420 may be an insulating material with a thermal conductivity less than about 0.05 Watts/Meter K.

The heat exchanging interface 420 may also include at least one sensing element (not shown) proximate to the heat exchanging interface 420. The sensing element, for example, may be generally flush with the heat exchanging interface 420. Alternatively, it may be recessed or protrude from the surface. The sensing element may include a temperature sensor, a pressure sensor, a transmissivity sensor, a bio-resistance sensor, an ultrasound sensor, an optical sensor, an infrared sensor, a sensor for measuring blood flow, or any other desired sensor. In one embodiment, the sensing element may be a temperature sensor configured to measure the temperature of the heat exchanging interface 420 and/or the temperature of the skin of the subject. For example, the temperature sensor may be configured as a probe or as a needle that penetrates the skin during measurement. Examples of suitable temperature sensors include thermocouples, resistance temperature devices, thermistors (e.g., neutron-transmutation-doped germanium thermistors), and infrared radiation temperature sensors. In another embodiment, the sensing element may be an ultrasound sensor configured to measure the thickness of a fat layer in the subject or crystallization of subcutaneous fat in the treatment region of a subject. In yet another embodiment, the sensing element may be an optical or infrared sensor configured to monitor an image of the treatment region to detect, for example, epidermal physiological reactions to the treatment. In yet another embodiment, the sensing element may be a device to measure blood flow. The sensing element may be in electrical communication with the processing unit 114 via, for example, a direct wired connection, a networked connection, and/or a wireless connection.

The vacuum device 160 may further include a mounting element 406 that couples the treatment units 408a, 408b to the vacuum device 160. The mounting element 406, for example, may be a bracket, frame or other suitable fixture. The treatment units 408a, 408b may include a heat sink 402 with a cover 401, and a thermoelectric cooler 404 disposed between the heat sink 402 and the heat exchanging interface 420. The thermoelectric cooler 404 may be a single Peltier-type element or a plurality of Peltier-type elements. One suitable thermoelectric cooler is a Peltier-type heat exchanging element (model # CP-2895) produced by TE Technology, Inc. in Traverse City, Mich.

In the illustrated embodiment, the heat sink 402 includes a serpentine shaped fluid conduit at least partially embedded in the heat sink 402. In the illustrated embodiment, the heat sink includes fluid ports 410a, 410b that may be coupled to a circulating fluid source (not shown) via the fluid lines 108a-b. In other embodiments, the heat sink 402 may include a plate-type heat exchange, a tube and a shell heat exchanger, and/or other types of heat exchanging devices.

Vacuum pressure may be supplied by any pump (e.g., pump 407 shown in FIG. 4B) capable of creating a pressure differential. Air pressure can either be controlled with a regulator between the vacuum source and the applicator, or pressure may be reduced up to the maximum capacity of the pump. For example, systems incorporating a regulator immediately downstream of the pump are designed to eliminate the regulator by sizing a pump with an appropriate maximum pressure capacity. According to one embodiment, approximately 5 inches Hg of vacuum is applied; in alternative embodiments, higher or lower vacuum levels are applied. In this embodiment, if the vacuum level is too low, the tissue will not be drawn adequately (or at all) inside reservoir 430 of the vacuum device 160; if the vacuum level is too high, undesirable discomfort to the patient and/or tissue damage could occur.

By alternating between two different vacuum levels inside the vacuum device 160, the force applied to the tissue will concomitantly increase and decrease, having the effect of a massaging action on the tissue. This may be accomplished, for instance, by ensuring the minimum vacuum level is high enough to keep the tissue drawn into the vacuum device 160, and have the tissue drawn further inside vacuum device 160 when the higher vacuum level is applied. If the tissue is drawn inside the applicator to the largest extent possible, friction between the walls of the applicator and the tissue may cause the tissue to maintain its overall position or assist the tissue in maintaining such a position. The change in vacuum pressure level at a desired frequency pulses the tissue, moving the area of tissue exposed to the vacuum to alternating positions within vacuum device 160. This is possible in part because initially, a higher pressure differential is required to draw the tissue past the sealing surface of the reservoir 430 and up inside the reservoir 430; however, once the tissue has been drawn into place, the force (and therefore the vacuum level) required to hold the tissue in place is lower. In this embodiment, the lower vacuum level (nearer to ambient pressure) may be very low, potentially as low as 1 inch of Hg or lower. The higher pulsing pressure can be 2 inches of mercury vacuum or higher. In operations, increasing the difference between the two vacuum levels increases the massage force. Further, increasing the cycle rate between the two pressures increases the massage frequency. Accordingly, the tissue can be pulsed in the range of approximately 0.1 Hz or lower and 10 Hz or higher. It is also possible to select the two vacuum levels (and possibly other parameters such as frequency, etc.) sufficient to draw the tissue into the vacuum device reservoir 430 and to impart a massage or pulsatile effect to the tissue while keeping the tissue position relatively constant inside reservoir 430 as alternating levels of vacuum are applied. This may be accomplished, for example, by decreasing the relative difference between vacuum levels applied to the tissue but by keeping the lower vacuum level high enough to keep the tissue drawn into the reservoir 430 of vacuum device 160 during treatment.

One method of creating this pneumatic massaging action is with a variable speed pump. Using pressure feedback to control the pump speed, the pump may electronically be controlled between two different vacuum levels. According to this embodiment, there is a mechanical lag in the time it takes the pump to change speeds, therefore, this embodiment may not be capable of pulsing at a frequency as high as some of the other embodiments described herein. According to yet another embodiment, a large piston is coupled to the treatment device 104; the piston is driven back and forth, either pneumatically or mechanically, to create a pressure wave in the system.

In an alternate embodiment shown in FIG. 5, one pump, two regulators and a 3-way valve may be used to switch between the two regulators. Alternative embodiments may be created, for example, by removing the higher vacuum pressure regulator or moving the 3-way valve in front of the regulators. In yet another embodiment, the 3-way valve could be replaced with two 2-position valves. According to this embodiment, the valves are solenoid valves, however, according to further embodiments, pneumatically controlled valves could be used.

Alternately, as shown in FIG. 6, two pumps and two regulators may be used. According to aspects of this embodiment, the dynamic response of the system is improved. Further, this embodiment may optionally be coupled with pneumatic cylinders to improve the pneumatic response of the system and provide for higher massage frequencies. According to still further embodiments, the regulators may be removed to allow the pumps to operate to their maximum pressure capacities. Other embodiments include systems in which the regulators take on different positions relative to the pumps or those in which different types of regulators are used.

As shown in FIG. 7, a valve and a backpressure regulator may be installed in the system. In operation, when the valve is opened, the pressure in the system reduces to the pressure set by the regulator. According to further embodiments, the regulator may be removed and the valve may be controlled by the processing unit 114. Further, the valve may be opened and air can be vented through an orifice (not shown) to limit the flow rate. The valve could be closed when the lower pressure limit is reached as measured by the pressure transducer, and the system would be returned to the higher vacuum pressure by the pump. One advantage of this embodiment is that the pressure relief would occur very quickly, thus possibly affording higher massage frequencies, among other advantages.

The illustrated embodiments of the actuator 105 combined with the treatment device 104 can enhance disruption of adipose tissue cooled by an external skin treatment device. Further, the illustrated embodiment may reduce treatment time, reduce discomfort to the patient and increase efficacy of treatment. For example, in an alternative embodiment, the vacuum device 160 may be employed without any vibratory, pulsing, or massage effect on the tissue drawn therein; rather, the vacuum may statically draw tissue into the reservoir 430 of the vacuum device 160, and hold the tissue in the reservoir 430 while cooling through a portion of or up to the entire duration of the treatment time, and releasing it only when the cooling treatment protocol is completed. Without being bound by theory, it is believed that while drawn into the vacuum device reservoir 430, the relative physical isolation of the target subcutaneous adipose tissue beneath the epidermis from the thermal mass of tissue normally below such tissue that is not drawn into reservoir 430 (e.g., underlying vasculature, muscles, etc.) and the reduction in blood circulation through the tissue drawn into reservoir 430 allow for a more efficient temperature reduction of lipid-rich cells such that the lipid-rich cells are substantially affected while non-lipid-rich cells in the epidermis are not substantially affected. This may have the advantage of increasing the efficacy of treatment and/or reducing treatment times.

F. Treatment Device Having a Plurality of Treatment Units

Figure 8:
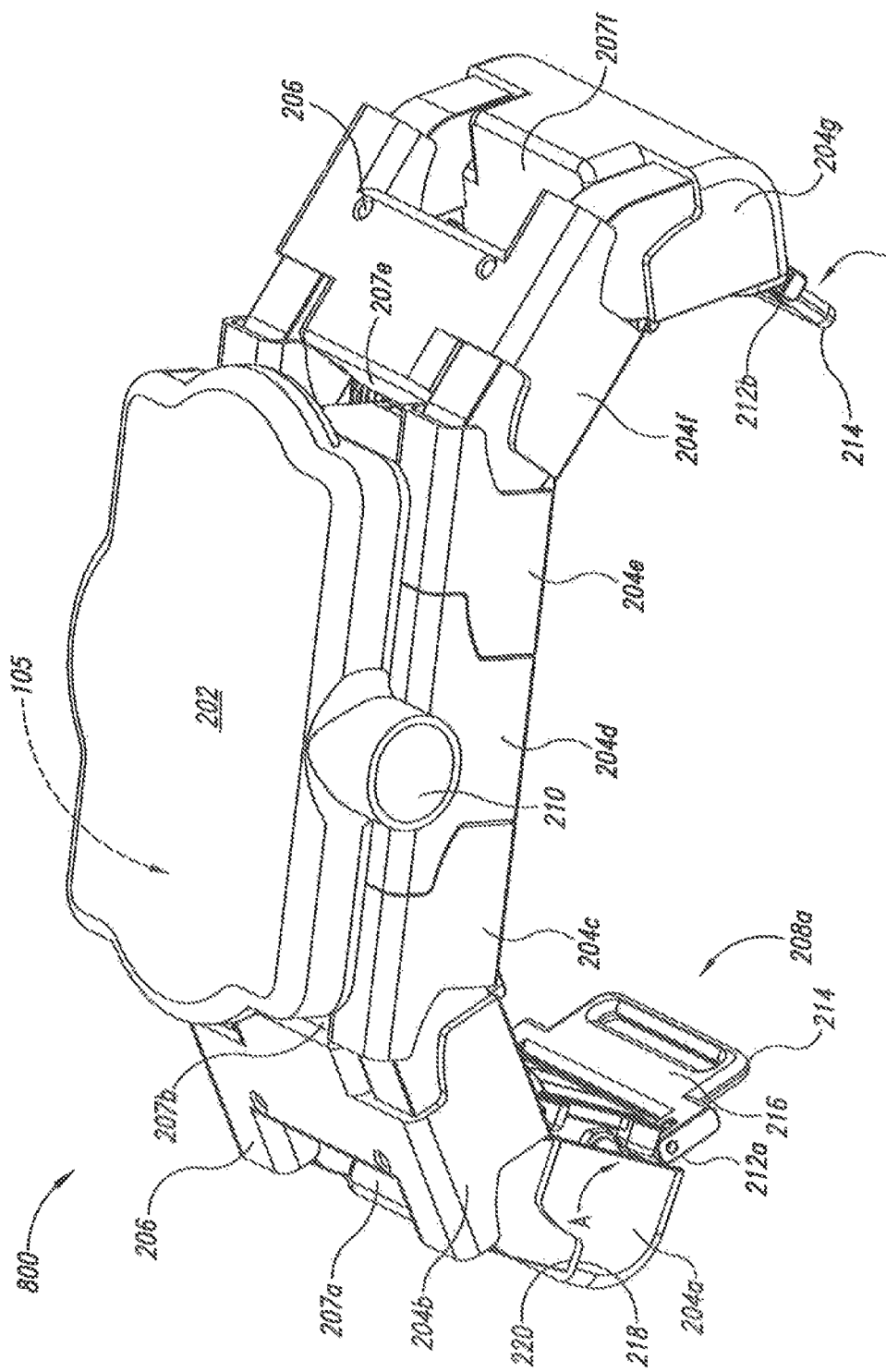
FIG. 8 is an isometric view of a treatment device for removing heat from subcutaneous lipid-rich cells in accordance with embodiments of the invention.

FIG. 8 is an isometric view of a treatment device 800 in accordance with a specific embodiment of a treatment device 800 for use with an actuator 105. In this embodiment, the treatment device 800 includes a control system housing 202 and treatment unit housings 204*a-g*. The actuator 105 may be coupled with, affixed to or contained within the control system housing 202 or the treatment unit housings 204*a-g*. The control system housing 202 includes a sleeve 308 (FIG. 9) that may slide into collar 310 and/or may mechanically attach to the treatment unit housings. The actuator 105 may further couple with, affix to, or be contained within, or encircle the sleeve 308.

The treatment unit housings 204*a-g* are connected to the heat exchanging elements (not shown) by attachment device 206. The attachment device may be any mechanical attachment device such as a screw or pin as is known in the art. The plurality of treatment unit housings 204*a-g* may have many similar features. As such, the features of the first treatment unit housing 204*a* are described below with reference symbols followed by an "a," corresponding features of the second treatment unit housing 204*b* are shown and noted by the same reference symbol followed by a "b," and so forth. The treatment unit housing 204*a* may be constructed from polymeric materials, metals, ceramics, woods, and/or other suitable materials. The example of the treatment unit housing 204*a* shown in FIG. 2A-C is generally rectangular, but it can have any other desired shape.

The control system housing 202 may house that actuator 105 and/or a processing unit for controlling the treatment device 800 and/or fluid lines 108*a-b* and/or electrical power and communication lines. The control system housing 202 includes a harness port 210 for electrical and supply fluid lines (not shown for purposes of clarity). The control system housing 202 may further be configured to serve as a handle for a user of the treatment device 800. Alternatively, a plurality of actuators (not shown) may be contained on any one of the treatment unit housing segments 204a-g.

As shown in FIG. 8, the treatment device 800 may further include at each end of the treatment device 800 retention devices 208a and 208b coupled to a frame 304. According to embodiments of the invention, the actuator 105 may further be coupled to the retention devices 208a and 208b. The retention devices 208a and 208b are rotatably connected to the frame by retention device coupling elements 212a-b. The retention device coupling elements 212a-b, for example, can be a pin, a ball joint, a bearing, or other type of rotatable joints.

The treatment device 104 includes a frame 304 having a plurality of rotatably connected segments 305a-g. The rotatably connected segments 305a-g are connected by hinges 306a-f, and, according to one embodiment, the actuator 105 is attached to at least one of the hinges 306a-f. Alternatively, the rotatably connected segments 305a-g of the frame 304 could be connected by a connection that allows rotation, such as a pin, a living hinge or a flexible substrate such as webbing or fabric or the like. According to one aspect of the invention, the links or hinges are made of plastic to insulate the treatment units from each other.

Figure 9:
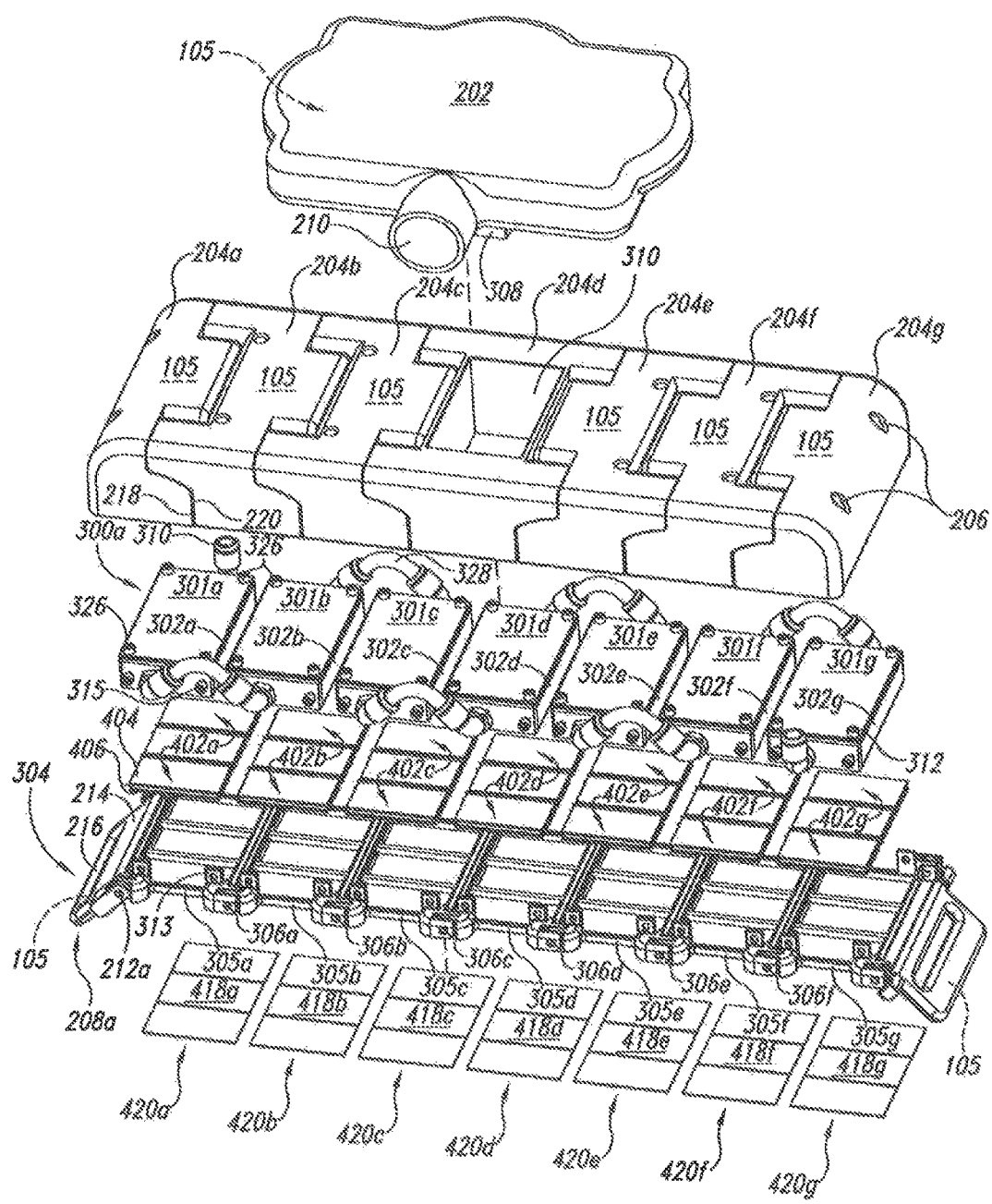
FIG. 9 is an exploded isometric view of the treatment device of FIG. 8 further illustrating additional components of the treatment device in accordance with another embodiment of the invention.

FIG. 9 is an exploded isometric view of the treatment device of FIG. 8 in accordance with one example of the invention for use in the system 100 as further described in U.S. patent application Ser. No. 11/528,225, which is herein incorporated in its entirety by reference. This further exploded view is substantially similar to previously described examples, and common acts and structures are identified by the same reference numbers. Only significant differences in operation and structure are described below. As can be appreciated by one skilled in the art, the actuator may be coupled to the treatment device at a variety of points; for example, the actuator may be contained within the housing, coupled to an outer surface of the housing, affixed to the frame at the hinge or along a segment, coupled to the treatment units, or coupled by any combination of connection points by any appropriate connection means as are known in the art.

Figure 10:
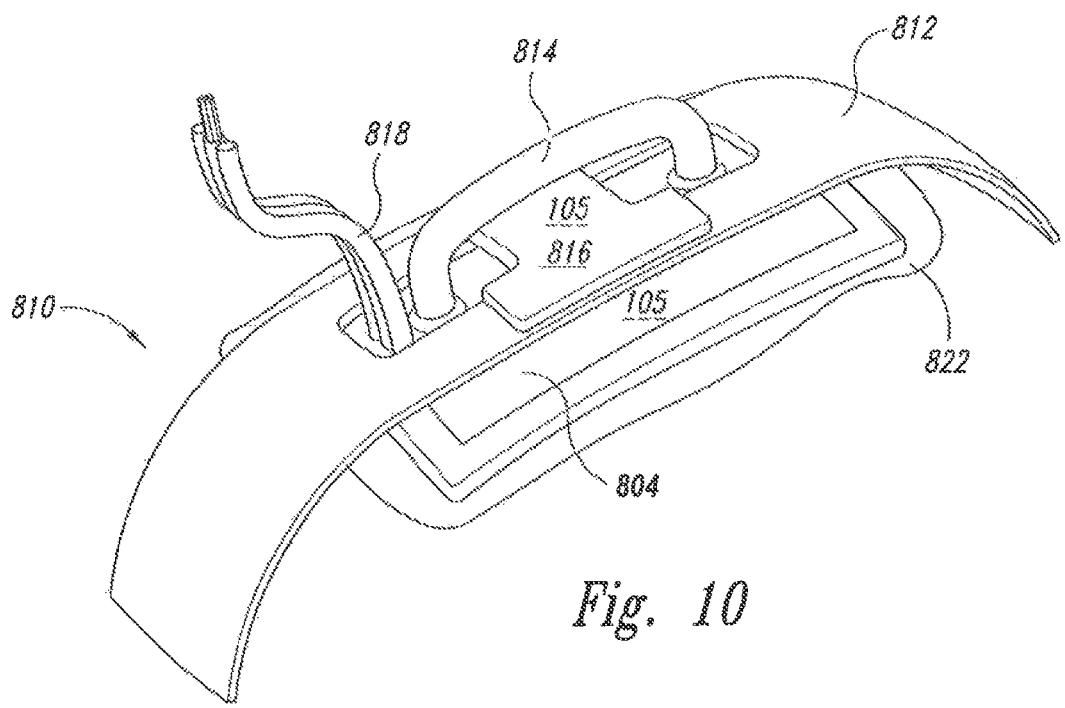
FIG. 10 is an isometric top view of an alternative treatment device for removing heat from subcutaneous lipid-rich cells in accordance with an embodiment of the invention.
Figure 11:
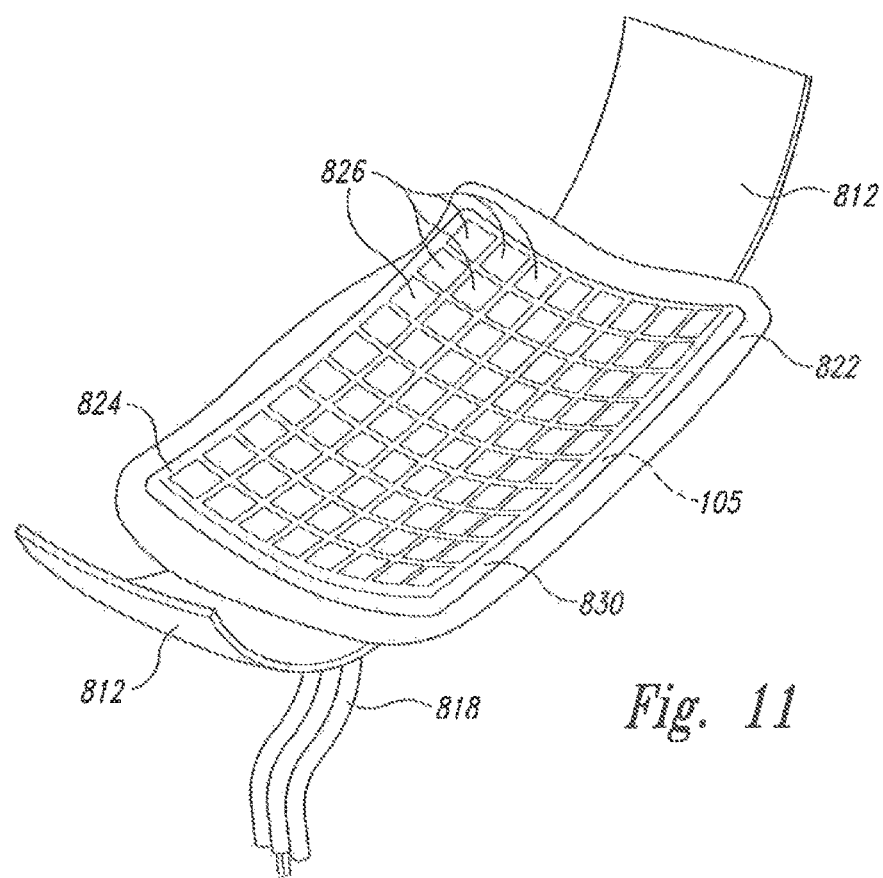
FIG. 11 is an isometric bottom view of the alternative treatment device of FIG. 10.

FIG. 10 is an isometric view of a plurality of thermoelectric coolers contained in a matrix design according to yet another treatment device that may be used with an actuator. As shown in FIGS. 10 and 11, the treatment device 810 includes a treatment unit 804 configured in a planar matrix 824 of thermoelectric coolers 826. According to one embodiment, the actuator 105 may be integral to the planar matrix 824, may attach to a portion of the planar matrix 824 or may be releasably coupled to the planar matrix 824. The treatment device 810 may further include a band 812 for retaining the treatment unit 804 in place during use and the actuator can be contained within or coupled to the band 812. The treatment device may further include a handle 814, a wiring harness 818 and a flap 816 for releasably securing the band 812 to the treatment unit 804. The actuator 105 may be contained within or coupled to the handle 814, wiring harness 818 and/or flap 816.

G. Operation of the Treatment Device

Without being bound by theory, it is believed that in operation effective cooling from the treatment device, which cools through conduction, depends on a number of factors. Exemplary factors that impact heat removal from the skin area and related tissue are the surface area of the treatment unit, the temperature of the interface member and the mechanical energy delivered to the tissue.

According to illustrated embodiments, the actuator 105 and the treatment device 104 combine to enhance disruption of cooled adipose tissue. Further, the illustrated embodiments may provide reduced treatment time, reduced discomfort to the patient and increased efficacy of treatment.

The illustrated embodiments can provide the treatment device 104 and the actuator 105 which reduce subcutaneous lipid-rich cells generally without collateral damage to non-lipid-rich cells in the treatment region. In general, lipid-rich cells can be affected at low temperatures that do not affect non-lipid-rich cells. As a result, lipid-rich cells, such as subcutaneous adipose tissue, can be affected while other cells in the same region are generally not damaged even though the non-lipid-rich cells at the surface are subject to even lower temperatures. The mechanical energy provided by the actuator further enhances the affect on lipid-rich cells by disrupting the affected lipid-rich cells.

In alternative embodiments, a cryoprotectant is used with the treatment device to, among other advantages, prevent freezing of the tissue during treatment as is described in U.S. patent application Ser. No. 11/741,271, filed Apr. 27, 2007, and entitled "Cryoprotectant for use with a Treatment Device for Improved Cooling of Subcutaneous Lipid-Rich Cells," herein incorporated in its entirety by reference.

H. Spatially Controlled Treatment Unit Profile

According to aspects of the invention, a spatially controlled profile can provide more efficient cooling to the treatment region. The plurality of actuators and/or thermoelectric coolers allows the treatment device to accommodate spatial cooling. For example, actuators may be contained at the perimeter of the treatment device to provide additional mechanical energy (via increased amplitude, or intensity, or via a longer duration, or any combination thereof) than mechanical energy provided by actuators contained at the interior of the treatment device because of different boundary conditions in the different areas of the treatment zone. Alternatively, individual actuators, or groups of individual actuators, may be actuated at varying times or with varying frequency in any combination to provide a varying spatial profile of imparted mechanical energy over the treatment region.

According to aspects of the invention, the device can accommodate spatially controlled treatment profiles which may provide at least the following advantages: (1) increased efficiency; (2) decreased power consumption with comparable efficacy; (3) increased patient comfort; or (4) decreased treatment time. For example, according to aspects of the invention, the plurality of actuators will allow adjustment for anatomical differences between patients by selectively enabling or disabling portions of the apparatus based on anatomical differences of the patient. This selective enablement may be accomplished by varying both the mechanical actuation mechanism and/or the cooling profile in any number of ways.

For instance, another alternative involves the implementation of a particular pattern of controlled cooling which may be customized to match an individual patient's pattern of cellulite, or subcutaneous fat, thus increasing the efficacy of the treatment and allowing the "sculpting" or contouring of the patient's tissue to achieve a desired aesthetic or other effect. Similarly, treatment regions requiring a higher intensity of treatment may be pre-identified by ultrasound or other devices. The device can then be spatially controlled to provide higher intensity treatment to those pre-identified areas. Further advantages include increased patient comfort and safety by allowing spatial control of cooling to accommodate special features of a particular patient's anatomy (e.g., lumps such as lipomas, blemishes or scars, areas having excess hair, areas containing implants or jewelry, or areas of heightened sensitivity such as nipples or wounds).

A further advantage of spatial control of the device includes utilizing only a subset of the actuators in order to treat only the region requiring treatment. It is advantageous to use one device that can accommodate small and large treatment regions without over treating (e.g. a large device that cannot be spatially controlled) or having to move the device multiple times thus extending the treatment time (e.g. a treatment device smaller than the treatment region). Thus, according to aspects of the invention, a selected region of actuators can be controlled to provide mechanical energy to select regions. Alternatively, a first actuator of the treatment device can be turned off while a second actuator of the treatment device is activated, such that only a selected region of the subject is treated with mechanical energy, thus limiting the treatment region. Other advantageous spatially controlled patterns include treating areas within the treatment region more intensely, conserving power by alternating actuators, increasing mechanical energy at a perimeter in order to provide a uniform energy distribution across the treatment area, and a combination of these spatially controlled patterns in order to increase treatment efficacy, reduce treatment time, decrease power consumption and provide for patient comfort and safety.

It is expressly understood that embodiments of the invention specifically contemplate utilizing, via spatial control or even a randomly selected profile, varying combinations of actuation to impart mechanical energy as described herein with applying treatment devices to affect the lipid-rich cells in any number of ways (e.g., varying frequency, intensity (amplitude), duration, start and stop times, temperature, etc.), applying mechanical energy alone without cooling, applying cooling alone without mechanical energy, utilizing reheating to accelerate damage to lipid-rich cells, to achieve the desired effect.

I. Method of Applying Treatment Devices

In one mode of operation, the actuator is coupled to a treatment device. The treatment device may be configured to be a handheld device such as the device disclosed in U.S. patent application Ser. No. 11/359,092, entitled "Treatment device For Removing Heat From Subcutaneous Lipid-Rich Cells", filed on Feb. 22, 2006, herein incorporated in its entirety by reference. The treatment device may be configured to be a plurality of treatment devices contained in a flexible substrate or in a rotatable housing such as the device disclosed in U.S. patent application Ser. No. 11/528,225, entitled "Cooling Devices Having a Plurality of Controllable Treatment units to Provide a Predetermined Cooling Profile", filed on Sep. 26, 2006, herein incorporated in its entirety by reference.

Applying the treatment device with pressure to the subject's skin or pressing against the skin can be advantageous to achieve efficient cooling. In general, the subject 101 has a body temperature of about 37° C., and the blood circulation is one mechanism for maintaining a constant body temperature. As a result, blood flow through the dermis and subcutaneous layer of the region to be treated may be viewed as a heat source that counteracts the cooling of the subdermal fat. As such, cooling the tissue of interest requires not only removing the heat from such tissue but also that of the blood circulating through this tissue. Thus, temporarily reducing or eliminating blood flow through the treatment region, by means such as, e.g., applying the treatment device with pressure, can improve the efficiency of tissue cooling and avoid excessive heat loss through the dermis and epidermis.

By cooling the subcutaneous tissue to a temperature lower than 37° C., subcutaneous lipid-rich cells can be selectively affected. In general, the epidermis and dermis of the subject 101 have lower amounts of unsaturated fatty acids compared to the underlying lipid-rich cells forming the subcutaneous tissues. Because non-lipid-rich cells usually can withstand colder temperatures better than lipid-rich cells, the subcutaneous lipid-rich cells can be selectively affected while maintaining the non-lipid-rich cells in the dermis and epidermis. An exemplary range for the treatment unit 302a-g can be from about −20° C. to about 20° C., preferably from about −20° C. to about 10° C., more preferably from about −15° C. to about 5° C., more preferably from about −10° C. to about 0° C.

The lipid-rich cells can be affected by disrupting, shrinking, disabling, destroying, removing, killing, or otherwise being altered. Without being bound by theory, selectively affecting lipid-rich cells is believed to result from localized crystallization of highly saturated fatty acids at temperatures that do not induce crystallization in non-lipid-rich cells. The crystals can rupture the bi-layer membrane of lipid-rich cells to selectively necrose these cells. Thus, damage of non-lipid-rich cells, such as dermal cells, can be avoided at temperatures that induce crystal formation in lipid-rich cells. Cooling is also believed to induce lipolysis (e.g., fat metabolism) of lipid-rich cells to further enhance the reduction in subcutaneous lipid-rich cells. Lipolysis may be enhanced by local cold exposure, inducing stimulation of the sympathetic nervous system.

Additional Embodiments of Treatment Device

Figure 12:
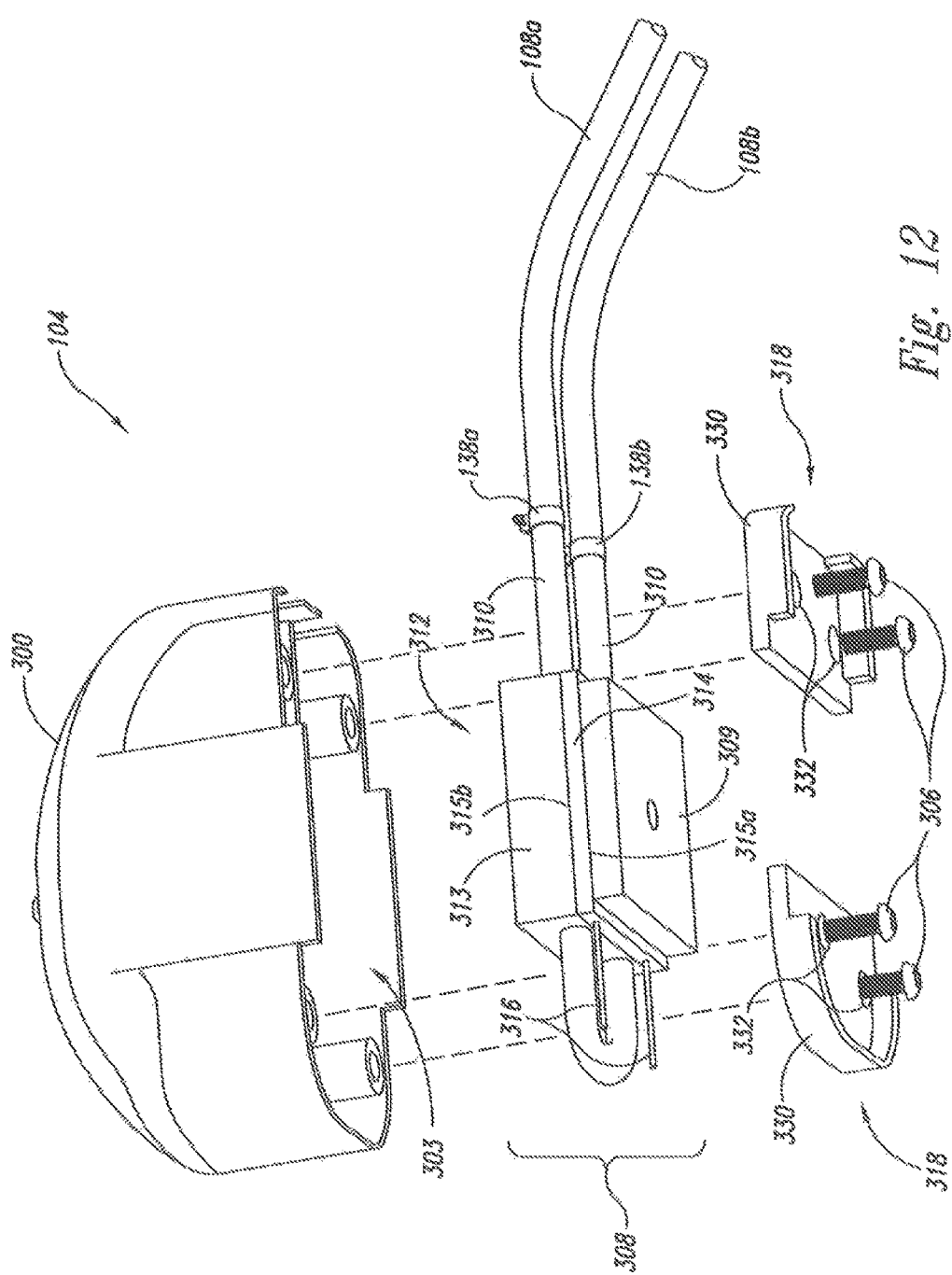
FIG. 12 is an isometric and exploded view of a treatment device for removing heat from subcutaneous lipid-rich cells in accordance with a further embodiment of the invention.

FIG. 12 is an isometric and exploded view of a treatment device 104 in accordance with another embodiment of the invention. The treatment device 104 may include a housing 300, a cooling assembly 308 at least partially disposed in the housing 300, and retention devices 318 configured for fastening the cooling assembly 308 to the housing 300. The treatment device 104 may also include a vibration member disposed in the housing 300, as described in more detail below with reference to FIG. 13.

The cooling assembly 308 may include a heat sink 312, a thermally conductive interface member 309, and a thermoelectric cooler 314 disposed between the heat sink 312 and the interface member 309. The thermoelectric cooler 314 may be connected to an external power supply (not shown) via connection terminals 316. In the illustrated embodiment, the heat sink 312 includes a U-shaped fluid conduit 310 at least partially embedded in a thermally conductive portion 313 of the heat sink 312. The fluid conduit 310 includes fluid ports 138a-b that may be coupled to a circulating fluid source (not shown) via the fluid lines 108a-b. In other embodiments, the heat sink 312 may include a plate-type heat exchanger, a tube and shell heat exchanger, and/or other types of heat exchanging device. The interface member 309 may include a plate constructed from a metal, a metal alloy, and/or other types of thermally conductive material. The thermoelectric cooler 314 may be a single Peltier-type element or an array of Peltier-type elements. One suitable thermoelectric cooler is a Peltier-type heat exchanging element (model # CP-2895) produced by TE Technology, Inc. in Traverse City, Mich.

Individual retention devices 318 may include a plate 330 and a plurality of fasteners 306 extending through a plurality of apertures 332 (two are shown for illustrative purposes) of the plate 330. In the illustrated embodiment, the fasteners 306 are screws that may be received by the housing 300. In other embodiments, the fasteners 306 may include bolts, clamps, clips, nails, pins, rings, rivets, straps, and/or other suitable fasteners. During assembly, the cooling assembly 308 is first at least partially disposed in the internal space 303 of the housing 300. Then, the retention devices 318 are positioned proximate to the cooling assembly 308, and the fasteners 306 are extended through the apertures 332 of the plate 330 to engage the housing 300. The fasteners 306, the plates 330, and the housing 300 cooperate to hold the cooling assembly 308 together.

By applying power to the thermoelectric cooler 314, heat may be effectively removed from the skin of the subject to a circulating fluid in the fluid conduit 310. For example, applying a current to the thermoelectric cooler 314 may achieve a temperature generally below 37° C. on the first side 315a of the thermoelectric cooler 314 to remove heat from the subject via the interface member 309. The thermoelectric cooler 314 transfers the heat from the first side 315a to the second side 315b. The heat is then transferred to the circulating fluid in the fluid conduit 310.

Figure 13:
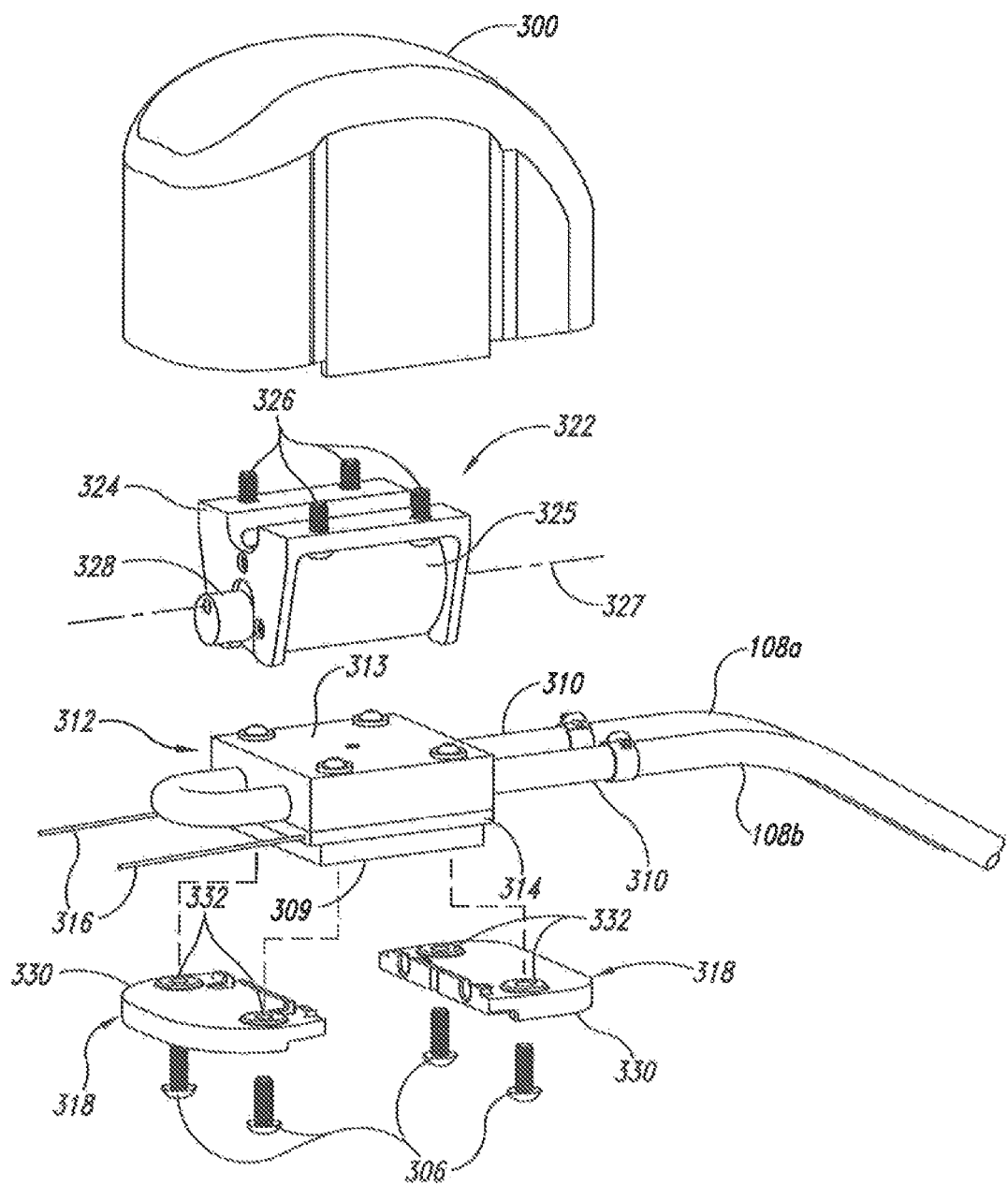
FIG. 13 is an isometric and exploded view of a vibrator disposed in the treatment device for removing heat from subcutaneous lipid-rich cells in accordance with yet another embodiment of the invention.

FIG. 13 is an isometric and exploded view of a vibrator 322 disposed in the treatment device 104 of FIG. 12. The vibrator 322 may include a frame 324, a motor 325 carried by the frame 324, a rotating member 328 operatively coupled to the motor 325, and a plurality of fasteners 326 (e.g., screws) for fixedly attaching the frame 324 to the housing 300. In the illustrated embodiment, the motor 325 has an output shaft (not shown) generally centered about a body axis 327 of the motor 325. One suitable motor is a direct current motor (model # Pittman 8322S008-R1) manufactured by Ametek, Inc., of Harleysville, Pa. The rotating member 328 has a generally cylindrical shape and is off-centered from the body axis 327. In other embodiments, the motor 325 may have an off-centered shaft that is operatively coupled to the rotating member 328.

In operation, applying electricity to the motor 325 may cause the rotating member 328 to rotate around the body axis 327 of the motor 325. The off-centered rotating member 328 causes the vibrator 322 to be off-balanced about the body axis 327, and vibration in the frame 324 and the housing 300 may result.

J. Computing System Software Modules

Figure 14:
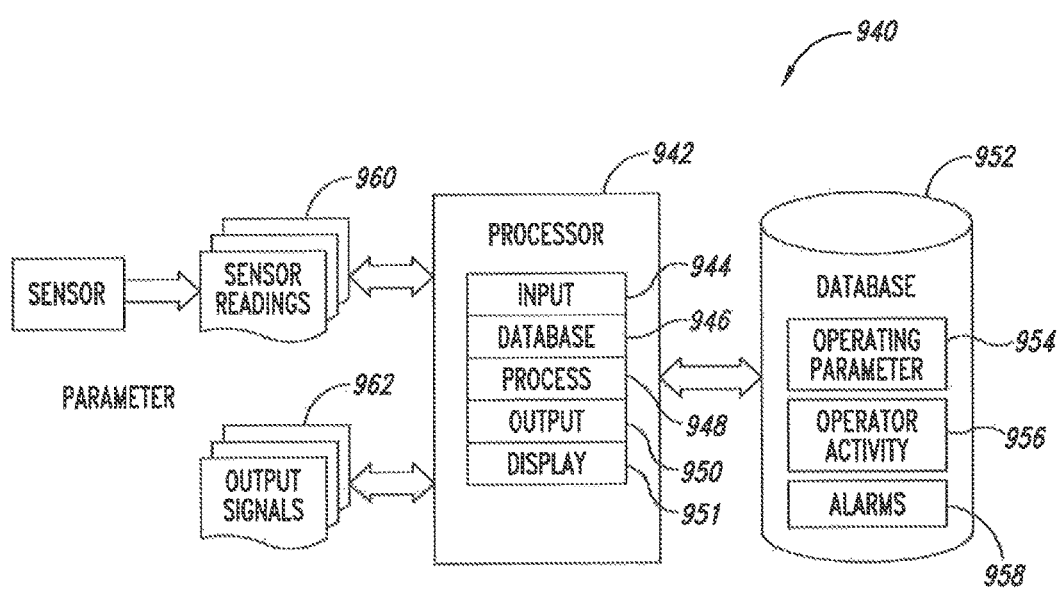
FIG. 14 is a block diagram showing computing system software modules for removing heat from subcutaneous lipid-rich cells in accordance with another embodiment of the invention.

FIG. 14 is a functional diagram showing exemplary software modules 940 suitable for use in the processing unit 114. Each component may be a computer program, procedure, or process written as source code in a conventional programming language, such as the C++ programming language, and can be presented for execution by the CPU of processor 942. The various implementations of the source code and object and byte codes can be stored on a computer-readable storage medium or embodied on a transmission medium in a carrier wave. The modules of processor 942 can include an input module 944, a database module 946, a process module 948, an output module 950, and, optionally, a display module 951. In another embodiment, the software modules 940 can be presented for execution by the CPU of a network server in a distributed computing scheme.

In operation, the input module 944 accepts an operator input, such as process setpoint and control selections, and communicates the accepted information or selections to other components for further processing. The database module 946 organizes records, including operating parameters 954, operator activities 956, and alarms 958, and facilitates storing and retrieving of these records to and from a database 952. Any type of database organization can be utilized, including a flat file system, hierarchical database, relational database, or distributed database, such as provided by a database vendor such as Oracle Corporation, Redwood Shores, Calif.

The process module 948 generates control variables based on sensor readings 960 (e.g., sensor readings from a sensor), and the output module 950 generates output signals 962 based on the control variables. For example, the output module 950 can convert the generated control variables from the process module 948 into 4-20 mA output signals 962 suitable for a direct current voltage modulator. The processor 942 optionally can include the display module 951 for displaying, printing, or downloading the sensor readings 960 and output signals 962 via devices such as the output device 120. A suitable display module 951 can be a video driver that enables the processor 942 to display the sensor readings 960 on the output device 120.

Unless the context clearly requires otherwise, throughout the description and the claims, the words "comprise," "comprising," and the like are to be construed in an inclusive sense as opposed to an exclusive or exhaustive sense; that is to say, in a sense of "including, but not limited to." Words using the singular or plural number also include the plural or singular number, respectively. When the claims use the word "or" in reference to a list of two or more items, that word covers all of the following interpretations of the word: any of the items in the list, all of the items in the list, and any combination of the items in the list.

U.S. patent application Ser. No. 11/750,953 and U.S. patent application Ser. No. 13/616,633 are incorporated by reference in their entireties. The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the invention can be modified, if necessary, to employ treatment devices and actuators with a plurality of treatment units, thermally conductive devices with various configurations, and concepts of the various patents, applications, and publications to provide yet further embodiments of the invention.

These and other changes can be made to the invention in light of the above-detailed description. In general, in the following claims, the terms used should not be construed to limit the invention to the specific embodiments disclosed in the specification and the claims, but should be construed to include all cooling that operates in accordance with the claims. Accordingly, the invention is not limited by the disclosure, but instead its scope is to be determined entirely by the following claims.

We claim:

1. A system for cooling and massaging a subject's tissue to damage subcutaneous lipid-rich cells, the system comprising:
    a vacuum device configured to receive the subject's tissue and including a vacuum cup defining a reservoir configured to receive the subject's tissue under vacuum;

at least one treatment unit coupled to the cup and including a first treatment unit positioned along a first wall of the vacuum cup and having a heat exchanging interface element and a thermoelectric cooler, the heat exchanging interface element is positioned to remove heat from the subject's tissue inside the reservoir when in use, a second treatment unit positioned along a second wall of the vacuum cup, wherein the first and second treatment units are positioned at opposite sides of the reservoir such that the entire thermoelectric cooler is positioned at one of the sides of the reservoir to cool the heat exchanging interface element, wherein a portion of the vacuum cup without a thermoelectric cooler extends circumferentially between the first and second treatment units, and wherein a flexible portion of the vacuum device is positioned to contact tissue within the reservoir;

an actuator including a vacuum pump and a pressure line fluidically coupling the vacuum pump to the vacuum cup; and a processing unit in communication with the actuator and the at least one treatment unit, wherein the processing unit is programmed to command the vacuum pump to operate to draw the subject's tissue into the reservoir and into thermal contact with the at least one treatment unit, command the at least one treatment unit to operate to cool and damage subcutaneous lipid-rich cells in the tissue held in the reservoir while the subject's non-lipid-rich cells proximate to the heat exchanging interface element are not significantly damaged; and after the subcutaneous lipid-rich cells are cooled and damaged, command the vacuum pump to adjust a pressure level in the reservoir between different pressure levels to massage the tissue inside the reservoir to further damage the subcutaneous lipid-rich cells in the tissue inside the reservoir.

2. The system of claim 1, wherein the processing unit is programmed to cause the actuator to adjust the pressure level in the reservoir at a frequency in a range of 0.1 Hz to 10 Hz.

3. The system of claim 1, wherein the at least one treatment unit includes a first treatment unit positioned along a first side wall of the vacuum cup, and a second treatment unit positioned along a second side wall of the vacuum cup, the first and second treatment units are positioned at opposites sides of the reservoir, wherein the processing unit is programmed to command the vacuum pump to operate to draw a fold of the tissue into the reservoir such that the subject's tissue is pulled into thermal contact with the first and second treatment units when in use.

4. The system of claim 1, further comprising:

a sensor positioned to detect the pressure level, and wherein the processing unit is operably coupled to the sensor and programmed to vary the pressure level inside the reservoir in response to one or more signals from the sensor.

5. The system of claim 1, wherein the processing unit is programmed to cause the vacuum pump to operate to impart oscillatory mechanical energy to a fold of the subject's tissue.

6. The system of claim 1, wherein the vacuum cup and the vacuum pump are configured to keep a fold of the tissue drawn into the reservoir while the fold of the tissue is massaged.

7. The system of claim 1, wherein at least one of the pressure levels is greater than one inch of mercury.

8. A system for cooling and damaging lipid-rich cells of a subject, the system comprising:

a cup having a wall defining an interior portion of the cup;

a plurality of treatment units attached to the cup, wherein each treatment unit of the plurality of treatment units has a heat exchanging interface in the wall of the cup and a thermoelectric cooler, wherein a portion of the cup extends circumferentially between two of the plurality of treatment unit positioned on opposite sides of the cup and is without any treatment unit, wherein the thermoelectric cooler is configured to reduce a temperature of a target region beneath an epidermis of the subject to reduce the temperature of lipid-rich cells in the target region, which is located within the cup, such that the lipid-rich cells are substantially affected while non-lipid-rich cells in the epidermis are not substantially affected; and a vacuum actuator configured to draw the lipid-rich cells in the target region at least partially into the cup, the vacuum actuator including:

a vacuum pump, and a vacuum line operably coupling the vacuum pump to the cup, such that the vacuum actuator is capable of imparting a massage effect to the lipid-rich cells in the target region; and a processing unit programmed to command the vacuum pump such that the vacuum pump operates to impart the massage effect to a fold of the subject's tissue held in the cup after the lipid-rich cells have been cooled and damaged to further damage the subcutaneous lipid-rich cells in the fold of the subject's tissue.

9. The system of claim 8, further comprising a sensor positioned to detect a vacuum level in the cup, the processing unit in communication with the sensor and the vacuum pump and programmed to vary the vacuum level between a first vacuum level of at least 2 inches of mercury and a second vacuum level, wherein the second vacuum level is at least 5 inches of mercury and is greater than the first vacuum level.

10. The system of claim 8, wherein at least one of the plurality of treatment units includes a heat sink having a fluid conduit configured to circulate a coolant.

11. The system of claim 8, further comprising:

a fluid source;

a heat sink; and a fluid line between the heat sink and the fluid source, wherein the heat sink is in fluid communication with the fluid source.

12. The system of claim 8, further comprising:

a sensor positioned to detect a pressure level within a reservoir in the cup, and wherein the processing unit is operably coupled to the sensor, the processing unit is programmed to vary a pressure level inside the reservoir in response to one or more signals from the sensor when the fold of the subject's tissue is located in the reservoir.

13. The system of claim 8, wherein the processing unit is programmed to cause the vacuum pump to operate to adjust a pressure in a reservoir in the cup to massage the fold of tissue.

14. A system for cooling and damaging lipid-rich cells of a subject, the system comprising:
- a cup having a wall defining an interior portion of the cup;
- a plurality of treatment units coupled to the cup, wherein each treatment unit of the plurality of treatment units has a heat exchanging interface in the wall of the cup and a thermoelectric cooler, wherein the thermoelectric cooler is configured to reduce a temperature of a target region beneath an epidermis of the subject to reduce the temperature of lipid-rich cells in the target region, which is located within the cup, such that the lipid-rich cells are substantially affected while non-lipid-rich cells in the epidermis are not substantially affected, wherein a portion of the cup without a thermoelectric cooler extends circumferentially between the heat exchanging interfaces located on opposite sides of a reservoir of the cup, wherein the entirety of each of the thermoelectric coolers is positioned alongside the reservoir; and
- a vacuum actuator configured to draw the lipid-rich cells in the target region at least partially into the cup, the vacuum actuator including:
  - a vacuum pump, and
  - a vacuum line operably coupling the vacuum pump to the cup, such that the vacuum actuator is capable of imparting a massage effect to the lipid-rich cells in the target region,
  - wherein the cup and the vacuum pump are configured to keep a fold of the subject's tissue drawn into the reservoir in the cup while imparting the massage to the fold of the tissue; and
- a processing unit programmed to command the vacuum pump such that the vacuum pump operates to adjust a pressure level in the reservoir between different pressure levels to impart the massage effect to the fold of the subject's tissue held in the reservoir after the lipid-rich cells have been cooled and damaged to further damage the subcutaneous lipid-rich cells in the fold of the subject's tissue, wherein at least one of the pressure levels is greater than one inch of mercury.

* * * * *